(12) United States Patent
Ogata et al.

(10) Patent No.: US 12,245,836 B2
(45) Date of Patent: Mar. 11, 2025

(54) INPUT DEVICE OF SURGICAL MANIPULATOR, ROBOT-ASSISTED SURGICAL SYSTEM, AND CONTROLLER

(71) Applicant: KAWASAKI JUKOGYO KABUSHIKI KAISHA, Kobe (JP)

(72) Inventors: Mariko Ogata, Kobe (JP); Hideki Tanaka, Nishinomiya (JP); Takeshi Kurihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 488 days.

(21) Appl. No.: 16/987,400

(22) Filed: Aug. 7, 2020

(65) Prior Publication Data

US 2021/0038336 A1 Feb. 11, 2021

(30) Foreign Application Priority Data

Aug. 8, 2019 (JP) ................. 2019-146233

(51) Int. Cl.
| | |
|---|---|
| *A61B 34/00* | (2016.01) |
| *A61B 17/00* | (2006.01) |
| *A61B 34/30* | (2016.01) |
| *A61B 34/37* | (2016.01) |
| *B25J 9/16* | (2006.01) |
| *F16H 1/14* | (2006.01) |

(52) U.S. Cl.
CPC .............. *A61B 34/77* (2016.02); *A61B 34/25* (2016.02); *A61B 34/30* (2016.02); *A61B 34/76* (2016.02); *B25J 9/1648* (2013.01); *A61B 2017/00973* (2013.01); *A61B 2034/305* (2016.02); *A61B 34/37* (2016.02); *A61B 34/74* (2016.02); *F16H 1/14* (2013.01)

(58) Field of Classification Search
CPC ......... A61B 34/77; A61B 34/25; A61B 34/30; A61B 34/76; A61B 34/37; A61B 34/74; A61B 2017/00973; A61B 2034/305; A61B 2017/00199; A61B 2017/00221; A61B 2034/2059; A61B 2090/067; B25J 9/1648; F16H 1/14
See application file for complete search history.

(56) References Cited

U.S. PATENT DOCUMENTS

| | | |
|---|---|---|
| 2002/0120363 A1 | 8/2002 | Salisbury et al. |
| 2017/0181805 A1* | 6/2017 | Nixon .................... A61B 34/71 |

(Continued)

*Primary Examiner* — Tammie K Marlen
*Assistant Examiner* — Ranjani Mari Sundaresan
(74) *Attorney, Agent, or Firm* — METROLEX IP LAW GROUP, PLLC; Robert L. Scott, Esq.

(57) ABSTRACT

An input device of a surgical manipulator includes an arm unit, a wrist unit including a follower link having a base end rotatably connected to a distal end of the arm unit around a follower rotation axis, a first gimbal link rotatably connected to the follower link, a second gimbal link rotatably connected to the first gimbal link, and an operation unit as a third gimbal link rotatably connected to the second gimbal link, a motor that rotates the base end of the follower link around the follower rotation axis, and a controller configured to perform feedback control of a rotation position of the follower link using a rotation position deviation of a rotation position of the second gimbal link with respect to a second reference rotation position as a rotation position deviation of the follower link by controlling an operation of the motor.

22 Claims, 14 Drawing Sheets

(56) References Cited

U.S. PATENT DOCUMENTS

2018/0036089 A1* 2/2018 Nakanishi ................ B25J 15/00
2019/0117310 A1* 4/2019 Hiratsuka .............. B25J 9/1689
2019/0133704 A1* 5/2019 Hiratsuka .............. A61B 34/37

* cited by examiner

[FIG. 1]
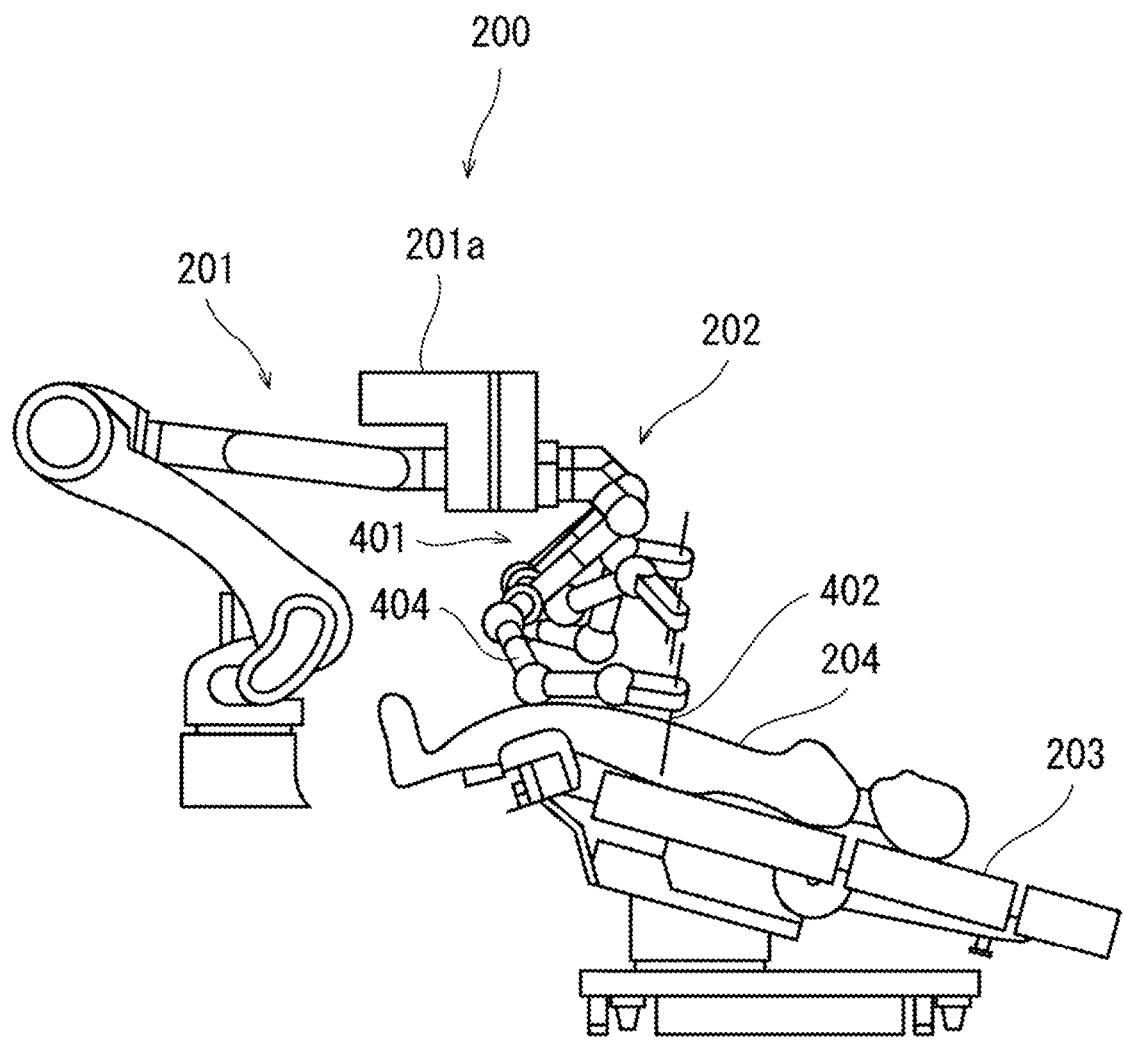

[FIG. 2]
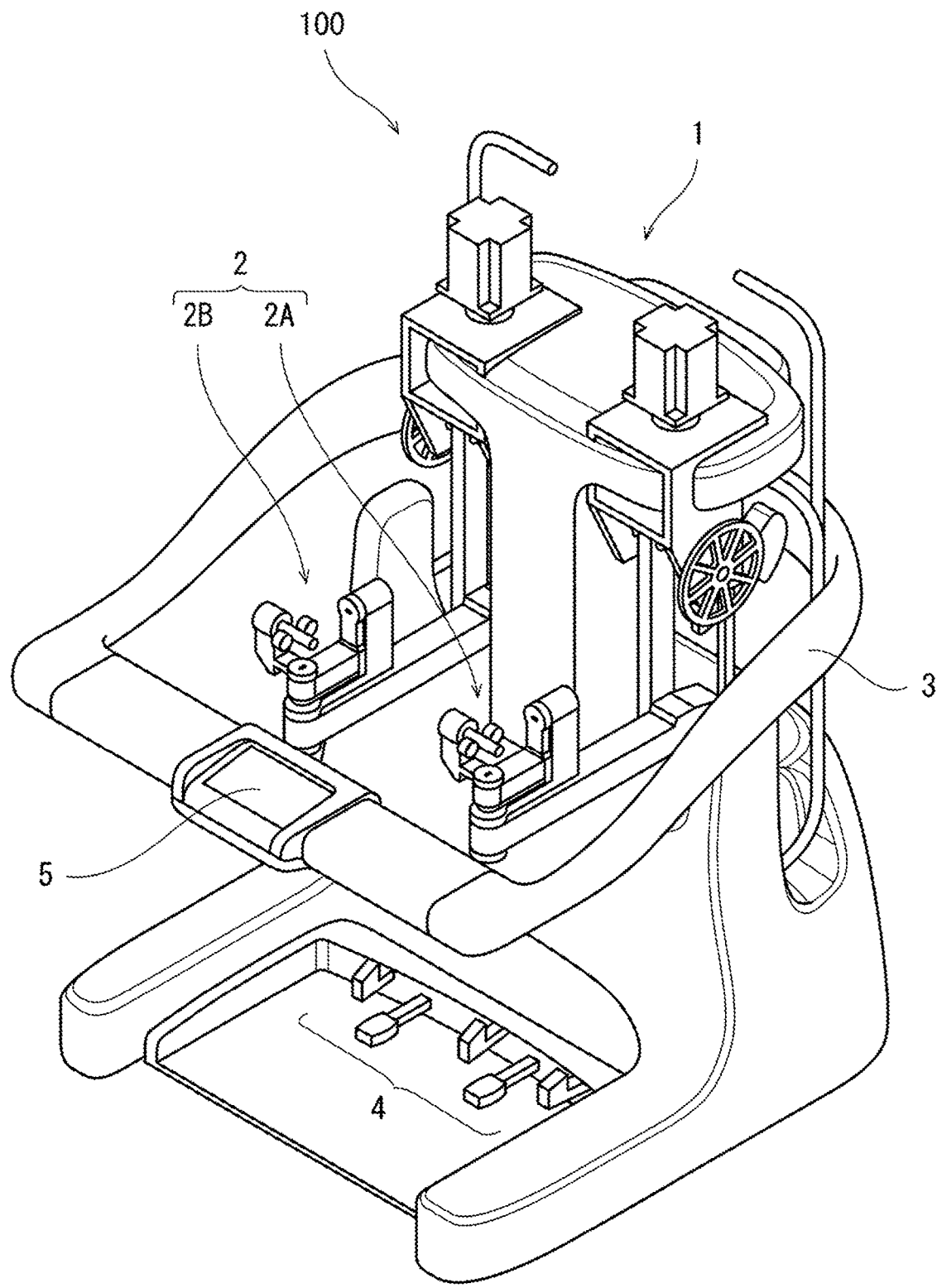

[FIG. 3]
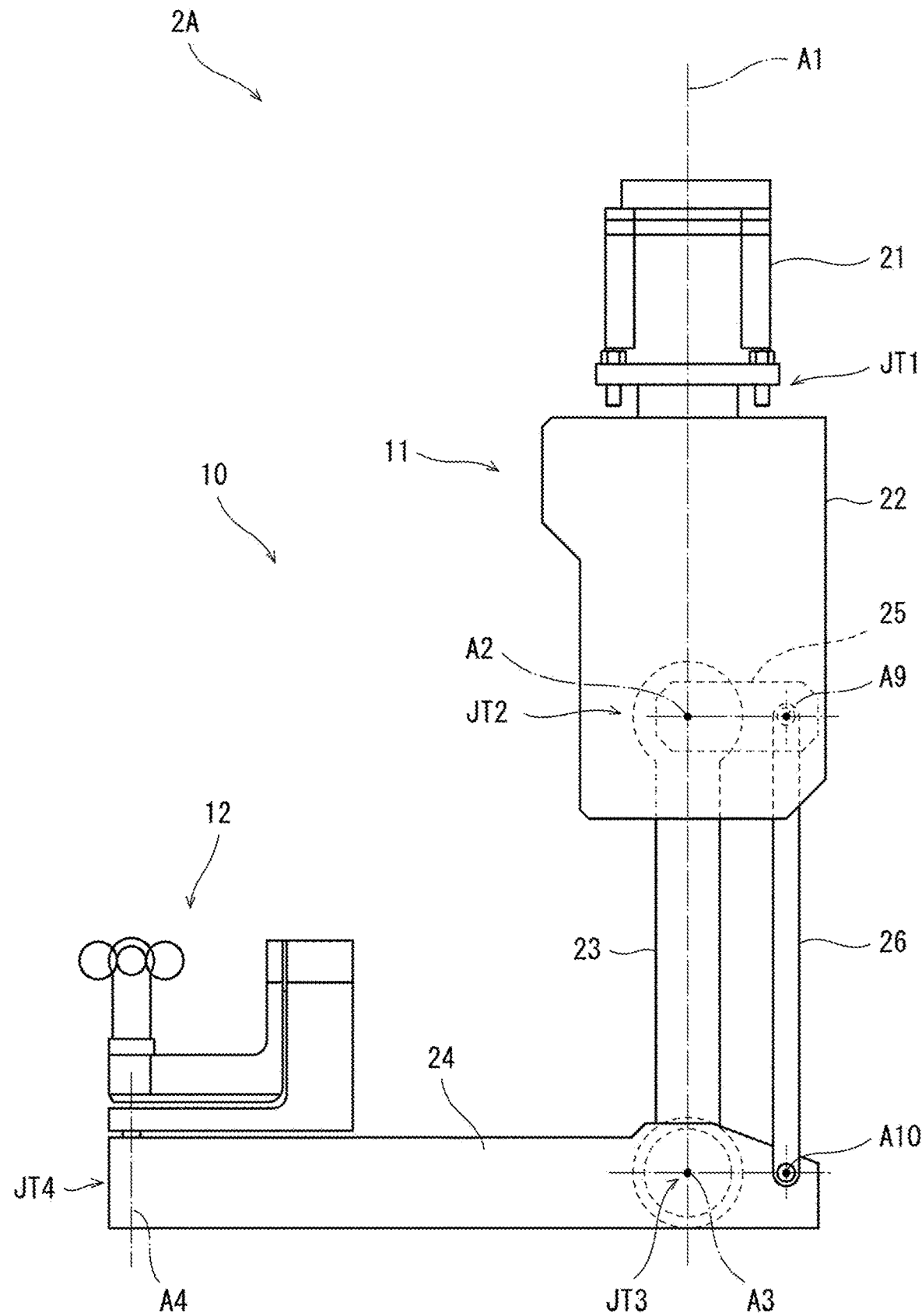

[FIG. 4]
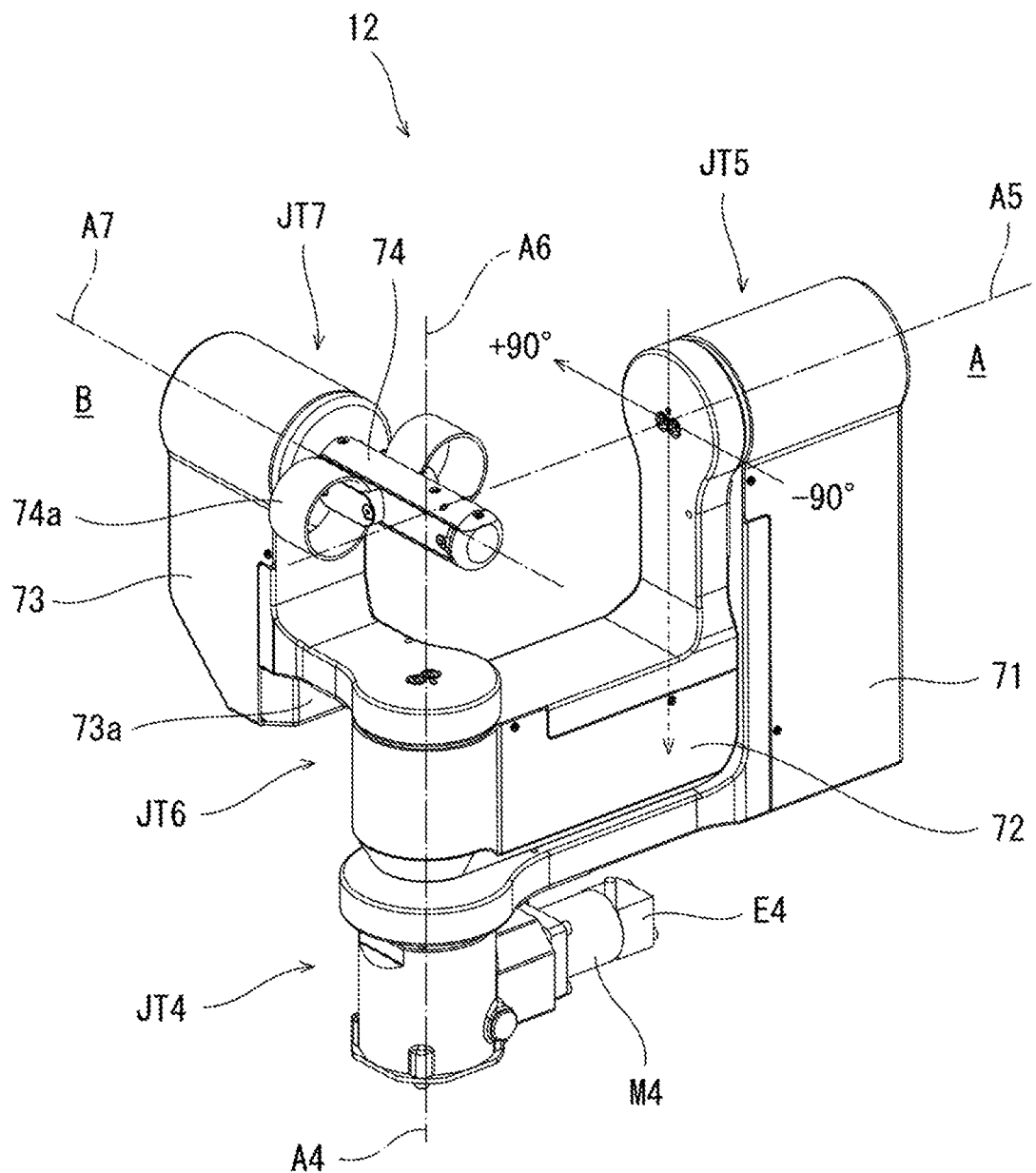

[FIG. 5]
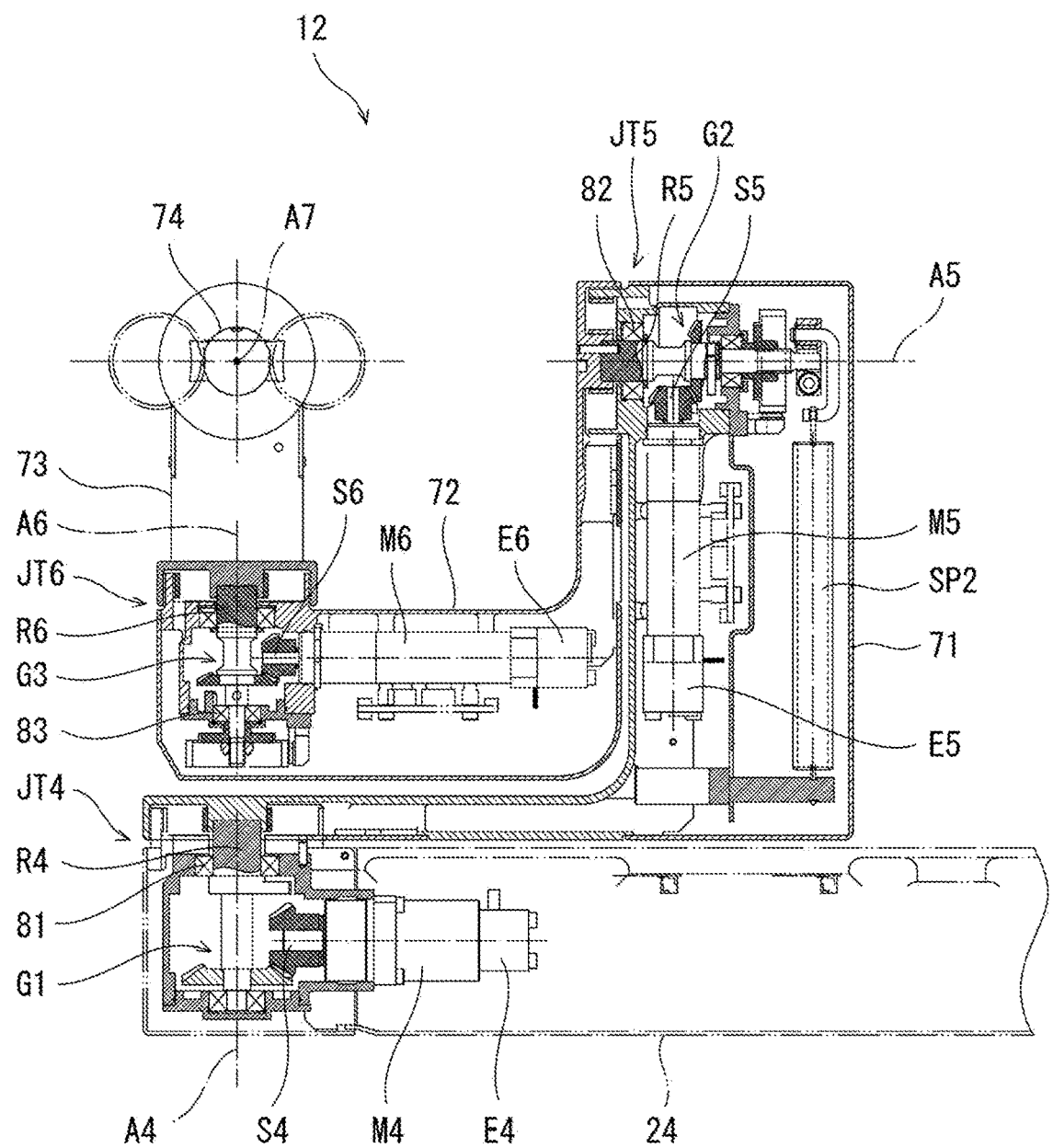

[FIG. 6]
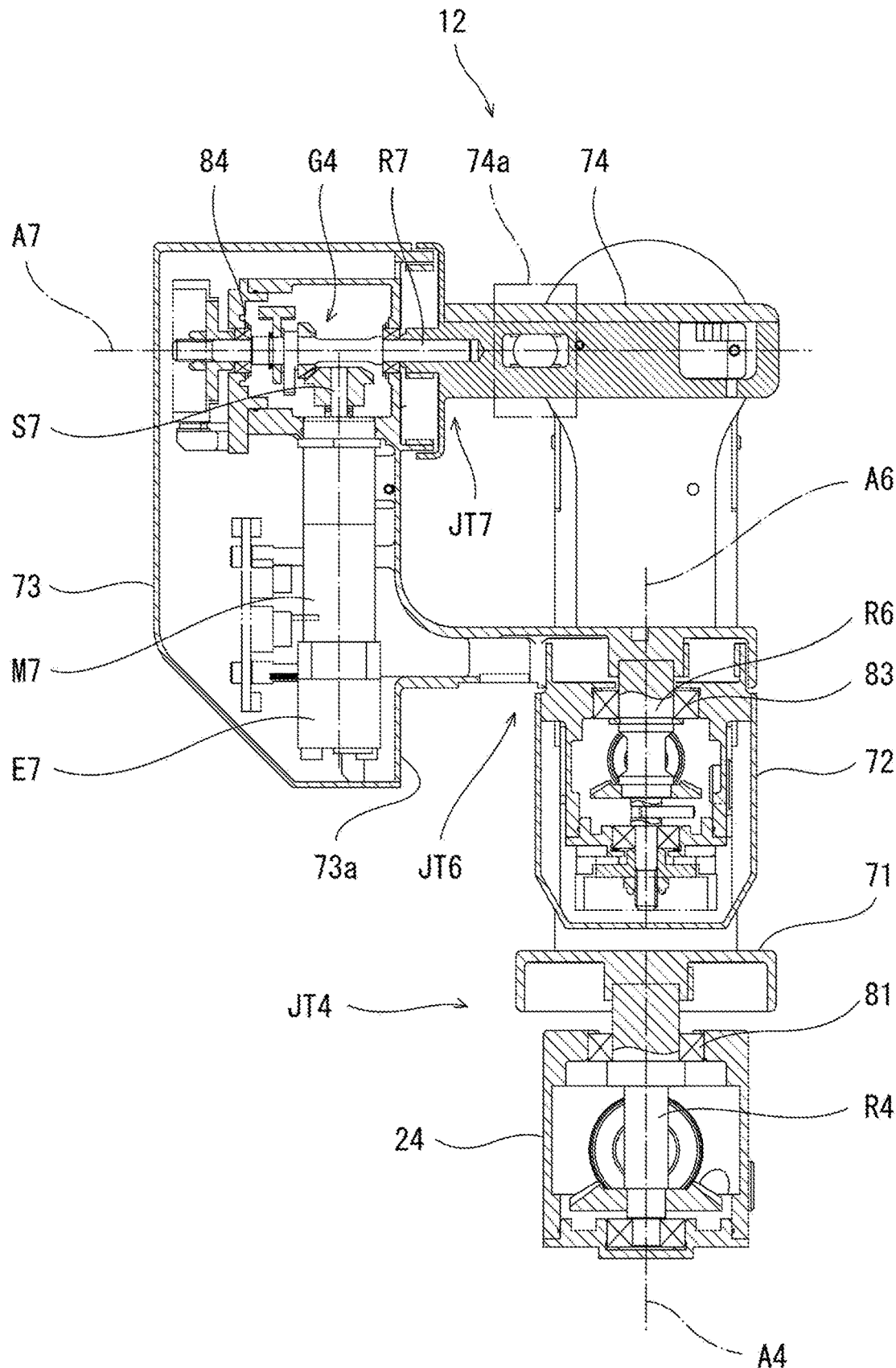

[FIG. 7]
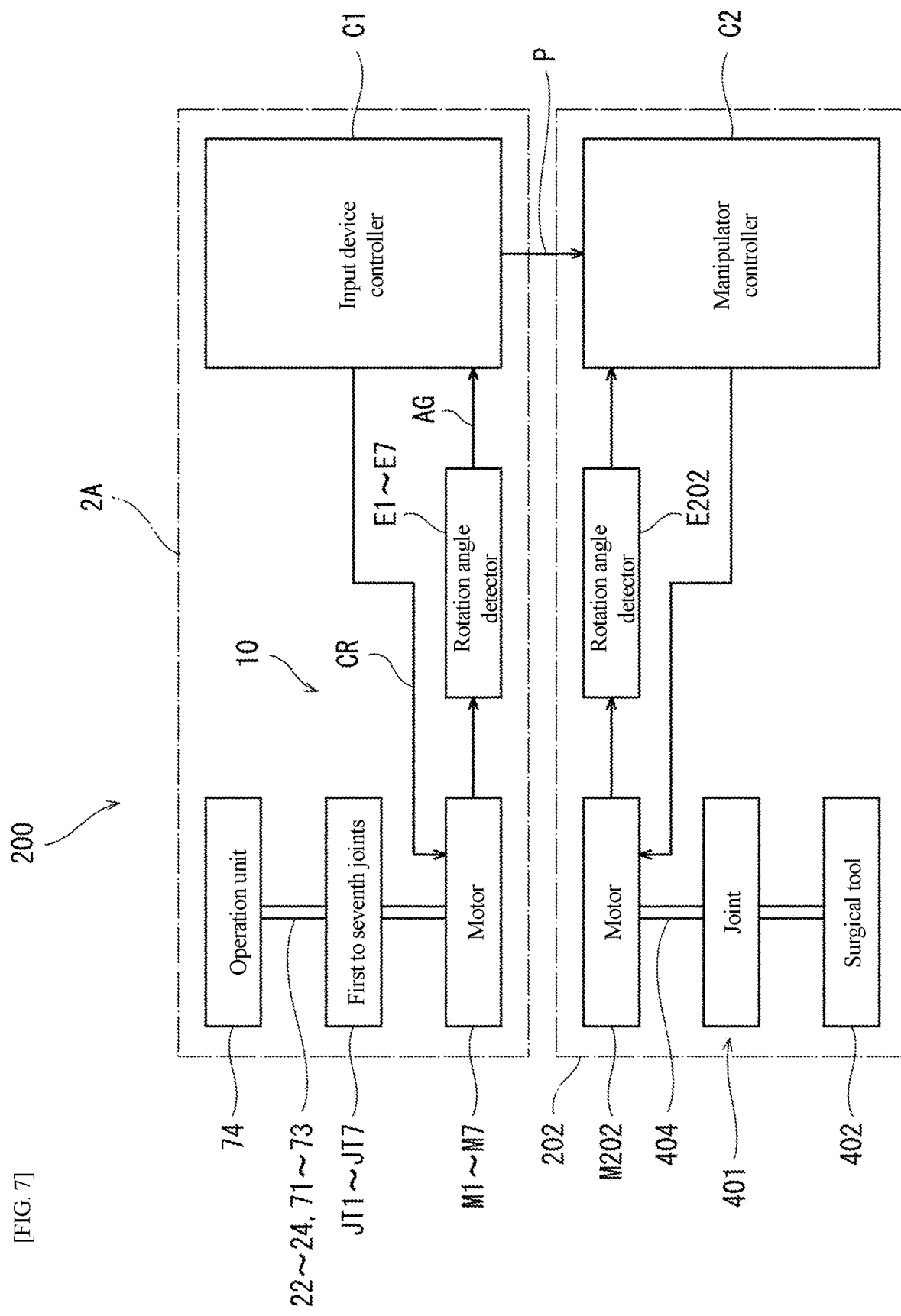

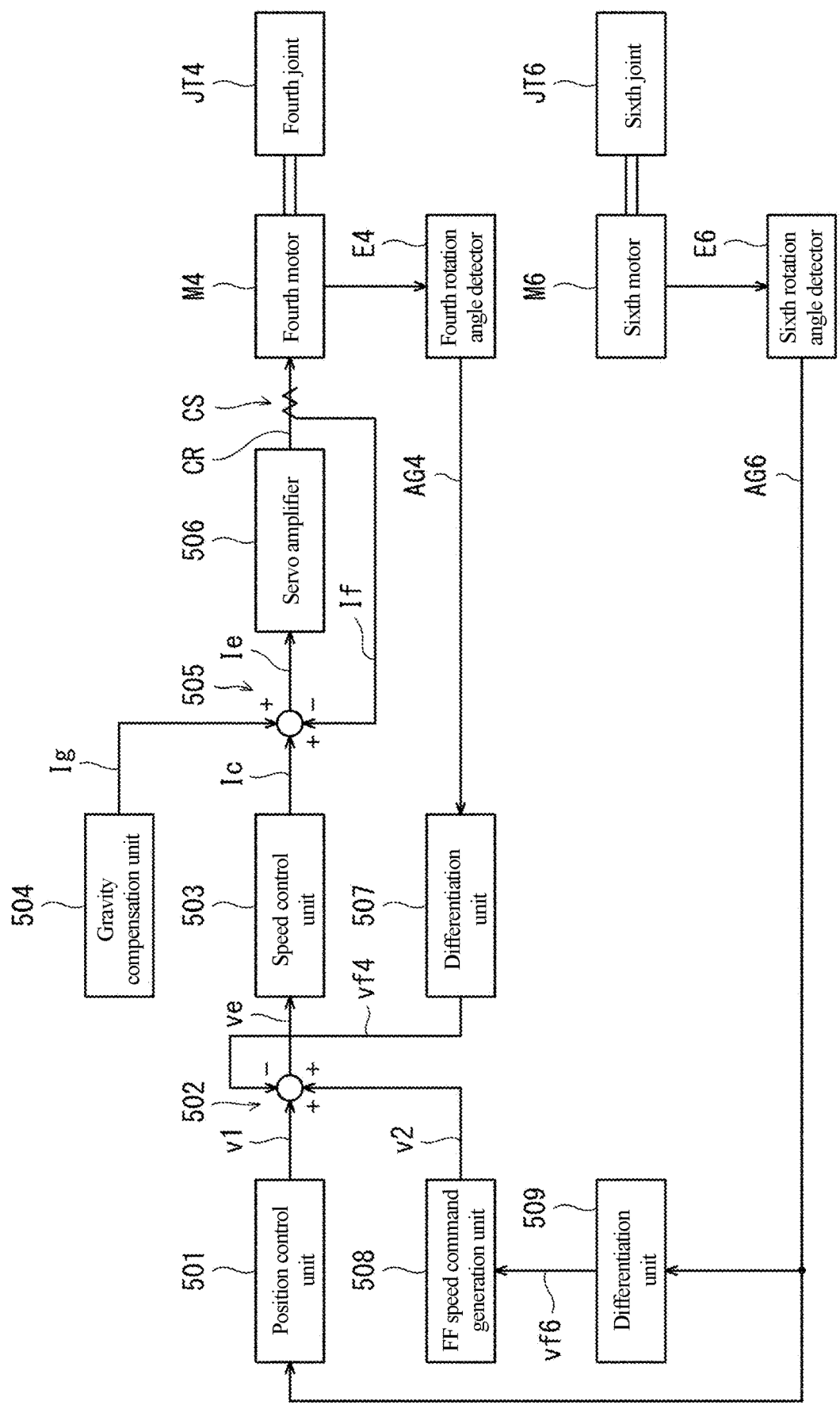
[FIG. 8]

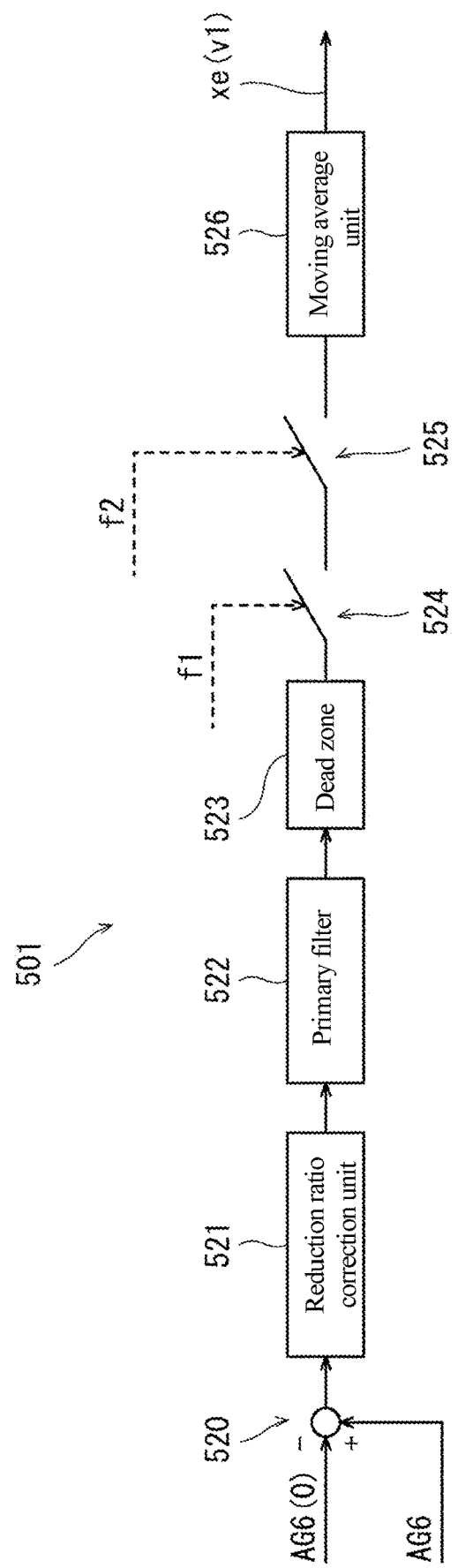
[FIG. 9]

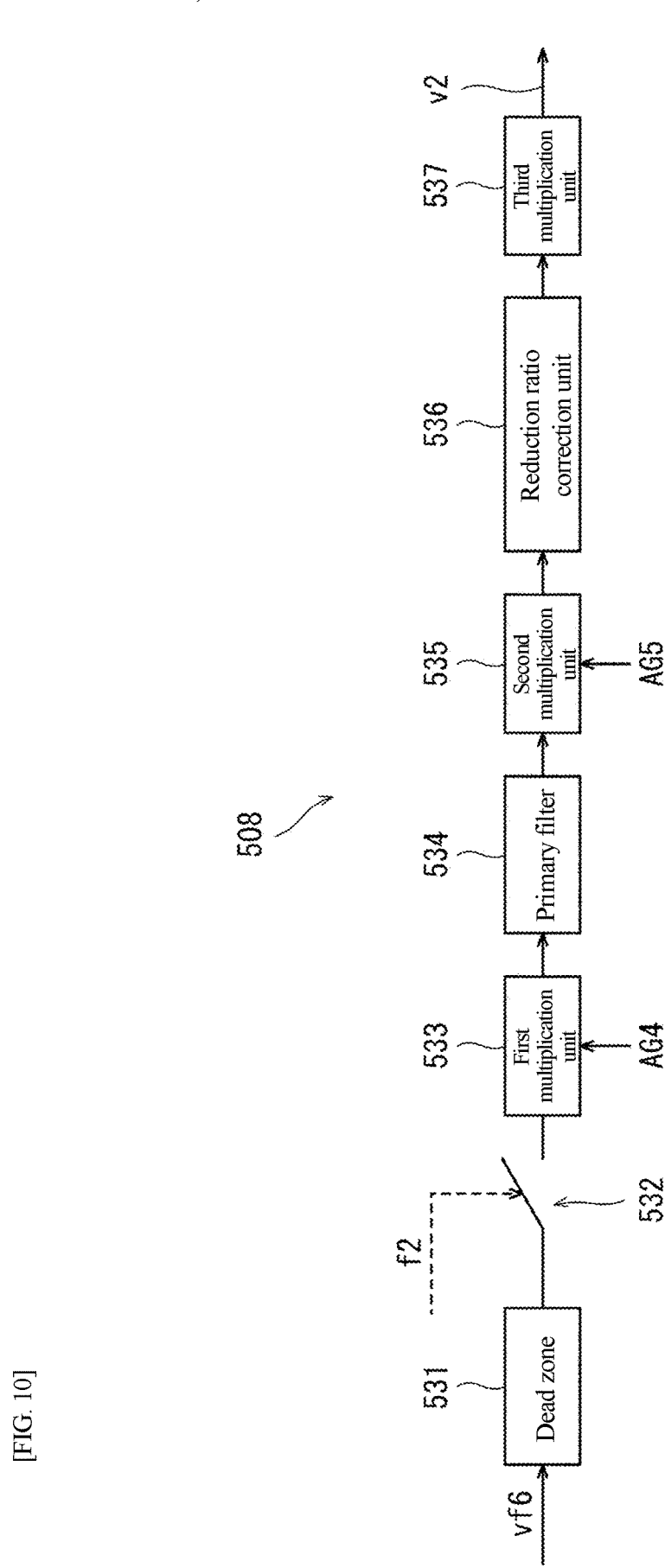
[FIG. 10]

[FIG. 11]
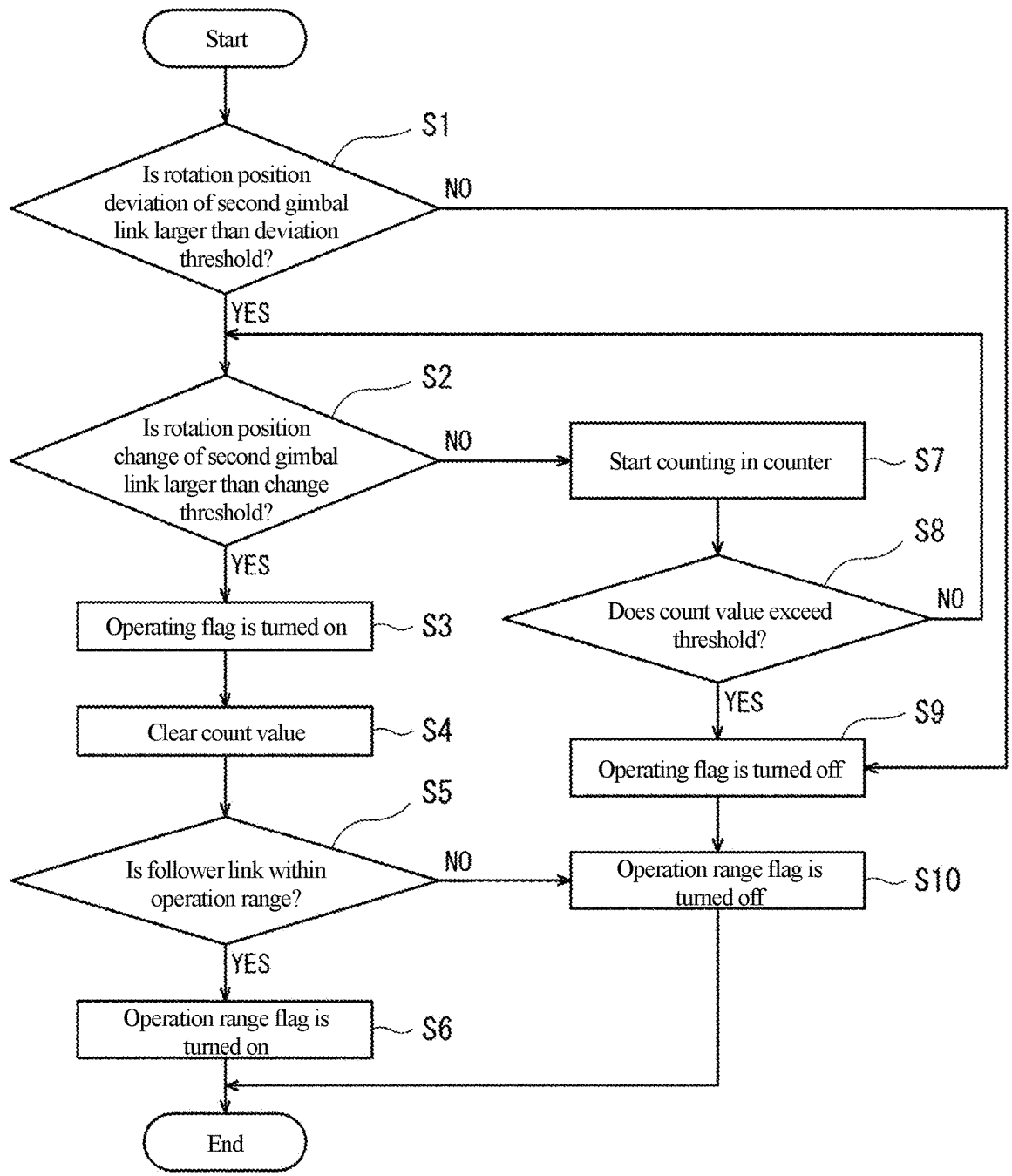

[FIG. 12]
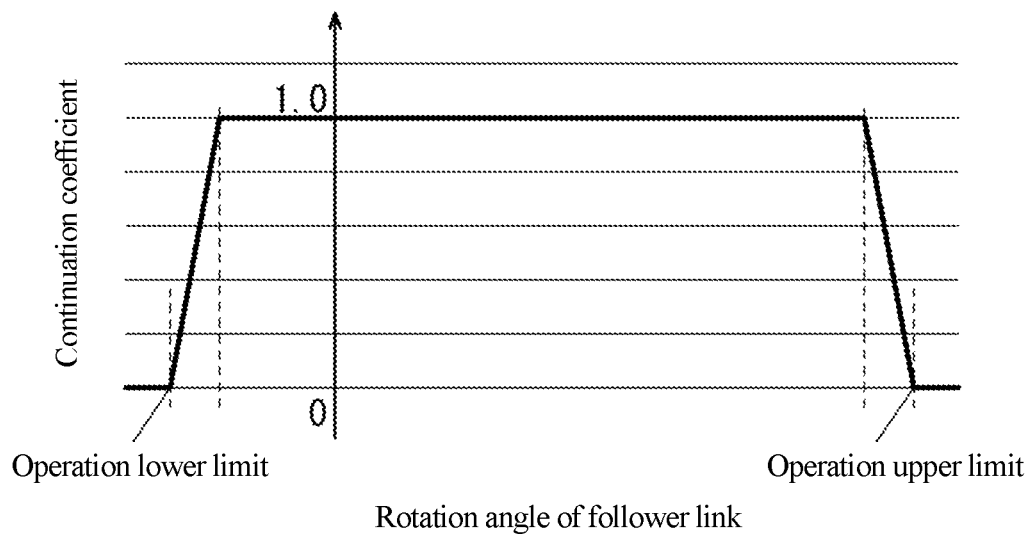
[FIG. 13]
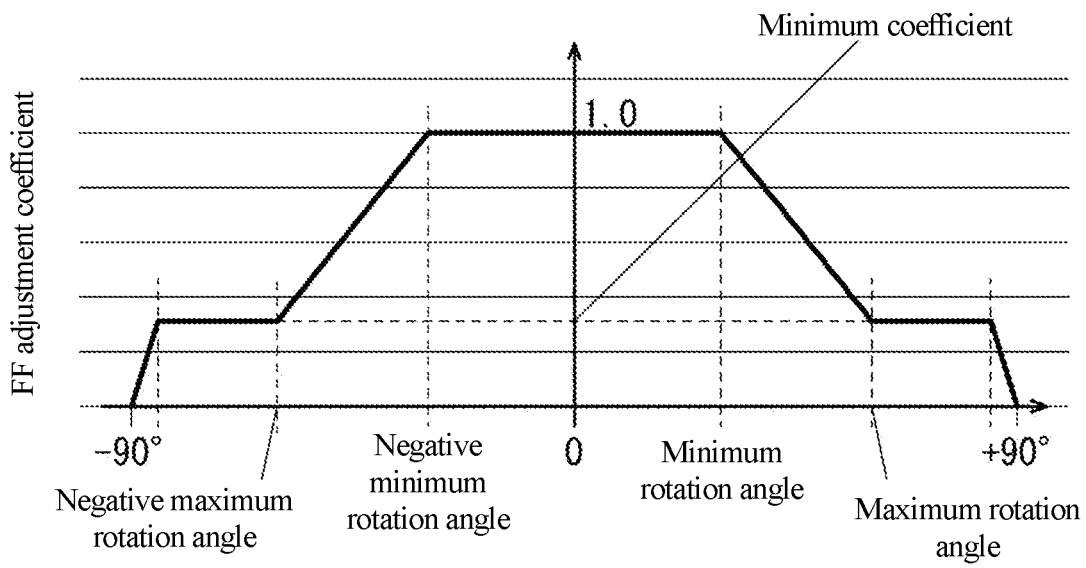

[FIG. 14]
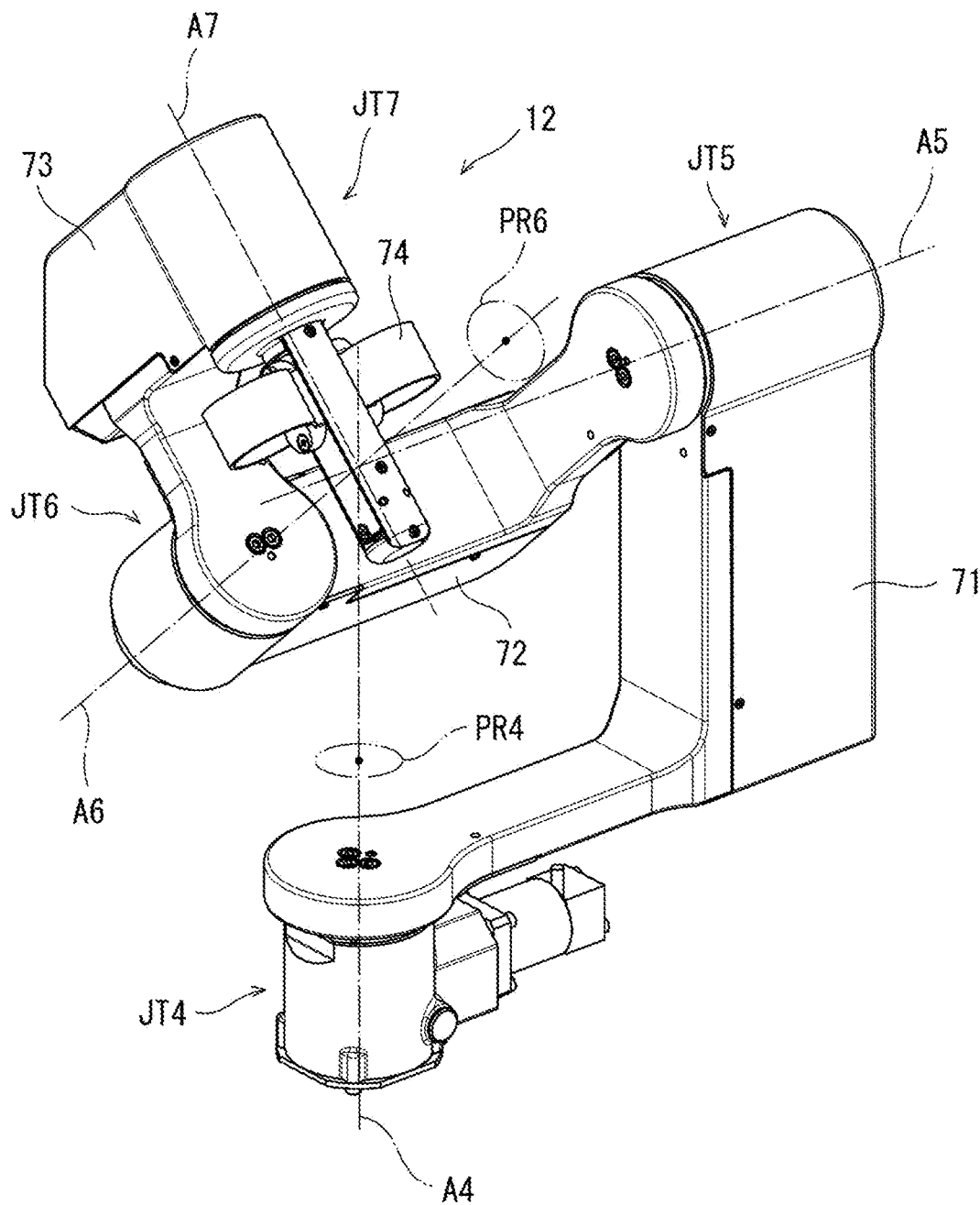

[FIG. 15]
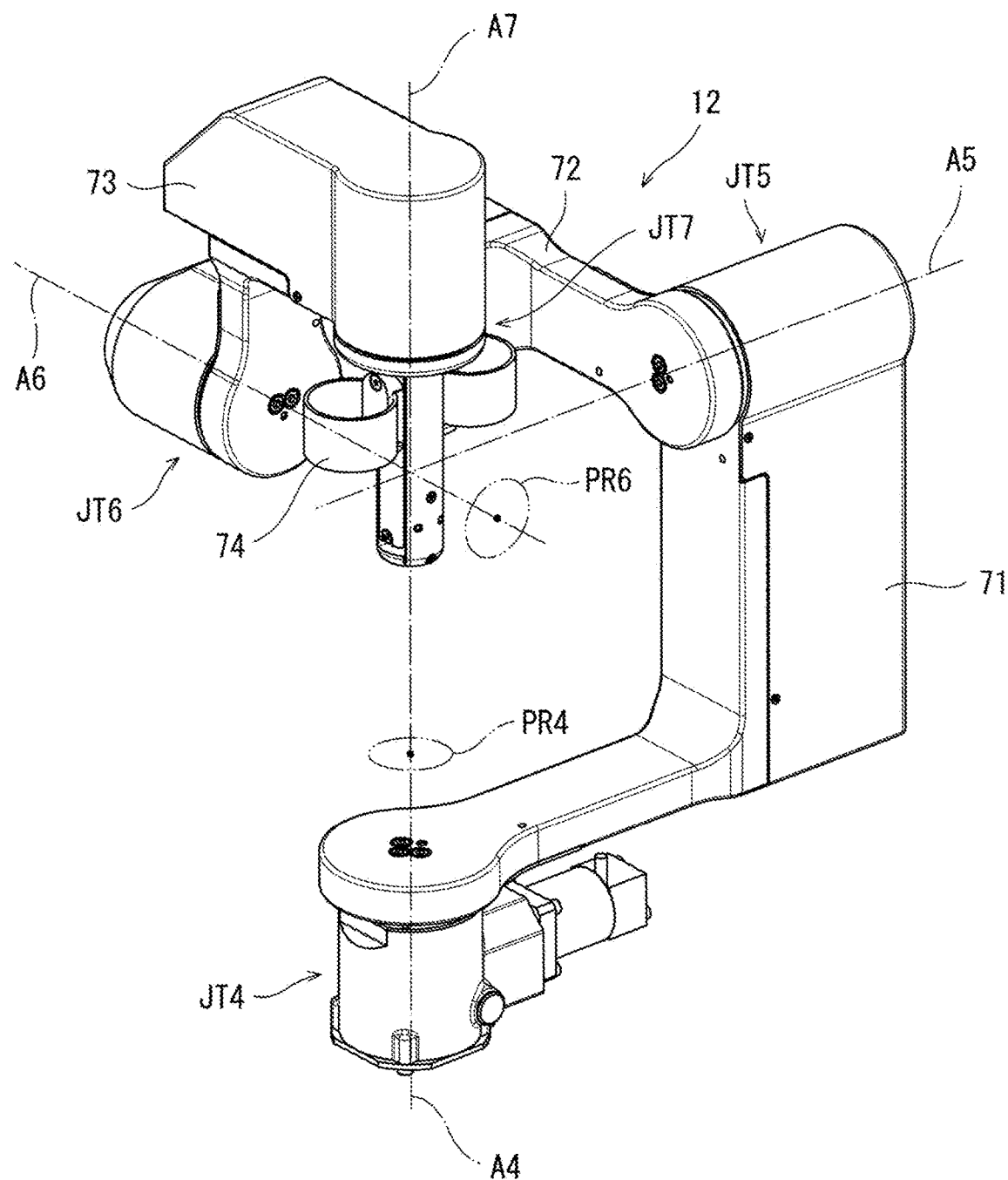

INPUT DEVICE OF SURGICAL MANIPULATOR, ROBOT-ASSISTED SURGICAL SYSTEM, AND CONTROLLER

BACKGROUND OF THE INVENTION

(1) Field of the Invention

The present invention relates to an input device of a surgical manipulator, a robot-assisted surgical system, and a controller.

(2) Description of Related Art

As an input device of a surgical manipulator, for example, a master device disclosed in US 2002/0120363 A1 is known. In this master device, a wrist is rotatably provided at a distal end of a three-axis arm. The wrist is located on a linkage having three axes (joints) configuring a gimbal having three degrees of freedom. A handle operated by an operator is located at a distal end of the three-axis linkage. Then, a processor controls each axis of the wrist to an angle close to a right angle by rotating the wrist with respect to the distal end of the arm on the basis of a rotation position of each axis (joint) of the wrist.

SUMMARY OF THE INVENTION

However, in the master device, the control is performed in order to prevent the linkage of the wrist from approaching a singularity. In this control, angular positions of the three axes of the wrist are controlled to minimize a cost, which is a function of a sum of the square of differences of current angular positions relative to nominal (preferred) angular positions of the three axes of the wrist.

In a genuine three-axis gimbal, support members configuring the gimbal of each axis are designed so as not to interfere with each other. However, in the wrist of the master device, when a first link rotates to near a second link, the first link interferes with the second link (see FIG. 1B of US 2002/0120363 A1). This is due to design constraints to provide a practical wrist. Also, a degree of interference depends on the design of the wrist.

On the other hand, in the master device, in order to prevent the linkage of the wrist from approaching the singularity, the angular positions of the three axes of the wrist are controlled to minimize the cost, which is the function of the sum of the square of differences of the current angular positions relative to the nominal (preferred) angular positions of the three axes of the wrist. Therefore, in the master device, there is no guarantee that interference between the links configuring the gimbal of the wrist can be prevented.

The present invention has been made to solve the above problems, and has an object to provide an input device of a surgical manipulator capable of preventing interference between links configuring a gimbal of a wrist unit, a robot-assisted surgical system including the input device, and a controller of the input device.

In order to achieve the above object, an input device of a surgical manipulator according to an aspect of the present disclosure includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, a motor that rotates the base end of the follower link around the follower rotation axis, and a controller configured to perform feedback control of a rotation position of the follower link using a rotation position deviation of a rotation position of the second gimbal link with respect to the second reference rotation position as a rotation position deviation of the follower link by controlling an operation of the motor.

A robot-assisted surgical system according to another aspect of the present disclosure includes a manipulator having a distal end to which a surgical tool is attached, and an input device that operates the manipulator, in which the input device includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, a motor that rotates the base end of the follower link around the follower rotation axis, and a controller configured to perform feedback control of a rotation position of the follower link using a rotation position deviation of a rotation position of the second gimbal link with respect to the second reference rotation position as a rotation position deviation of the follower link by controlling an operation of the motor.

A controller according to still another aspect is configured to control an input device that operates a manipulator having a distal end to which a surgical tool is attached, in which the input device includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, and a motor that rotates the base end of the follower link around the follower rotation axis, and the controller is configured to perform feedback control of a rotation position of the follower link using a rotation position deviation of a rotation position of the second gimbal link with respect to the second reference rotation position as a rotation position deviation of the follower link by controlling an operation of the motor.

The present disclosure can provide the input device of a surgical manipulator capable of preventing interference between the links configuring the gimbal of the wrist unit, the robot-assisted surgical system including the input device, and the controller of the input device.

BRIEF DESCRIPTION OF THE DRAWINGS

FIG. 1 is a schematic diagram showing an outline of an example of a robot-assisted surgical system including an input device of a surgical manipulator according to an embodiment of the present disclosure;

FIG. 2 is a schematic diagram showing an outline of an appearance of an example of a hand control included in the robot-assisted surgical system in FIG. 1;

FIG. 3 is a side view schematically showing an outline of the input device shown in FIG. 2;

FIG. 4 is a perspective view showing an appearance of a wrist unit of a master arm in FIG. 3;

FIG. 5 is a sectional view showing a vertical cross section of a follower link and a first gimbal link of the wrist unit in FIG. 4;

FIG. 6 is a sectional view showing a vertical cross section of a second gimbal link and an operation unit of the wrist unit in FIG. 4;

FIG. 7 is a functional block diagram showing an example of a configuration of a control system of the input device and the surgical manipulator;

FIG. 8 is a functional block diagram showing an example of a configuration of gimbal link interference prevention control of an input device controller in FIG. 7;

FIG. 9 is a block diagram showing a configuration of a position control unit in

FIG. 8;

FIG. 10 is a block diagram showing a configuration of an FF speed command generation unit in FIG. 8;

FIG. 11 is a flowchart showing the gimbal link interference prevention control;

FIG. 12 is a graph showing a relationship between a rotation angle of the follower link and a continuation coefficient of an input of speed feedforward control to a position feedback control loop;

FIG. 13 is a graph showing a relationship between a rotation angle of the first gimbal link and an FF adjustment coefficient of the input of the speed feedforward control to the position feedback control loop;

FIG. 14 is a perspective view showing a state of the wrist unit when the first gimbal link rotates +45° from a first reference rotation position; and FIG. 15 is a perspective view showing a state of the wrist unit when the first gimbal link rotates +90° from the first reference rotation position.

DETAILED DESCRIPTION OF PREFERRED EMBODIMENTS

An input device of a surgical manipulator according to an aspect of the present disclosure includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, a motor that rotates the base end of the follower link around the follower rotation axis, and a controller configured to perform feedback control of a rotation position of the follower link using a rotation position deviation of a rotation position of the second gimbal link with respect to the second reference rotation position as a rotation position deviation of the follower link by controlling an operation of the motor.

Here, the "rotation position" refers to a rotation angle. Hereinafter, the "rotation position" is used when a use of a concept of "position" facilitates understanding, and the "rotation angle" is used when a use of a concept of "angle" facilitates understanding.

In this configuration, by controlling the operation of the motor, the controller performs feedback control of the rotation position of the follower link using the rotation position deviation of the rotation position of the second gimbal link with respect to the second reference rotation position. Thus, the follower link rotates around the follower rotation axis to locate the second gimbal link at the second reference rotation position. Here, it is assumed that the first gimbal link extends on a plane A including the first gimbal rotation axis and the second gimbal rotation axis that are orthogonal to each other, and the second gimbal link extends on a plane B including the second gimbal rotation axis and the third gimbal rotation axis that are orthogonal to each other. It is also assumed that the second gimbal link interferes with the first gimbal link when the second gimbal link rotates near the first gimbal link. In this case, when the second gimbal link is located at the second reference rotation position, the plane B on which the second gimbal link extends is orthogonal to the plane A on which the first gimbal link extends. That is, an included angle between the second gimbal link and the first gimbal link is a right angle when viewed from an extending direction of the second gimbal rotation axis. Thus, even if the second gimbal link rotates toward the first gimbal link, the rotation of the follower link causes the first gimbal link to escape such that the included angle becomes a right angle, thereby preventing the second gimbal link from interfering with the first gimbal link.

The controller may be configured to determine whether the operation unit is operated, and to perform the feedback control upon determination that the operation unit is operated.

As described above, when the second gimbal link is rotated by the operation of the operation unit, the follower link is rotated to locate the second gimbal link at the second reference rotation position. If a slight rotation position deviation of the second gimbal link remains when the operation is stopped, the follower link continues to rotate and gives the operator discomfort.

This configuration can avoid such discomfort given to the operator with a configuration in which feedback control of the rotation position of the follower link is performed when the operation unit is in operation, and the feedback control of the rotation position of the follower link is stopped when the operation is stopped.

The controller may be configured to determine whether the follower link is within a predetermined operation range, and to perform the feedback control upon determination that the follower link is within the predetermined operation range.

This configuration can cause the follower link to follow within the predetermined operation range.

The controller may be configured to perform feedforward control of adding a rotation speed of the second gimbal link to a speed command in the feedback control of the rotation position of the follower link. Here, the "rotation speed" refers to "rotation angle speed". Hereinafter, the "rotation speed" is used when a use of a concept of "speed" facilitates understanding, and the "rotation angle speed" is used when a use of a concept of "angle" facilitates understanding.

In this configuration, the rotation speed of the second gimbal link is added to the speed command in the feedback control of the rotation position of the follower link. Thus, even if the second gimbal link operates at a high speed by operating the operation unit, the follower link can follow quickly to prevent interference between the second gimbal link and the first gimbal link.

The controller may be configured to determine whether the follower link is within a predetermined operation range, and to perform the feedforward control upon determination that the follower link is within the predetermined operation range.

This configuration can cause the follower link to follow within the predetermined operation range.

The controller may be configured to adjust an addition amount of a rotation speed of the second gimbal link to a speed command in the feedback control to gradually decrease as the follower link goes toward a predetermined operation range limit of the follower link, near the predetermined operation range limit of the follower link in the feedforward control.

This configuration can prevent a sudden change in an addition amount of the rotation speed of the second gimbal link by the feedforward control when the second gimbal link moves from the outside to the inside of the operation range, which gives the operator discomfort in the operation.

The controller may be configured to adjust an addition amount of a rotation speed of the second gimbal link to a speed command in the feedback control to decrease toward zero as an absolute value of a rotation position deviation with respect to the first reference rotation position of a rotation position of the first gimbal link approaches 90 degrees from 0 degrees in the feedforward control.

When the rotation angle of the first gimbal link from the first reference rotation position increases due to the operation of the operation unit, a rotation amount of the operation unit around the follower rotation axis accompanying the rotation of the second gimbal link from the second reference rotation position increases. When the rotation speed of the operation unit around the follower rotation axis is high at that time, the operator feels discomfort in the operation.

In this configuration, when the rotation angle of the first gimbal link from the first reference rotation position increases due to the operation of the operation unit, the rotation speed of the operation unit around the follower rotation axis is suppressed, thereby preventing the operator from feeling discomfort in the operation.

A robot-assisted surgical system according to another aspect of the present disclosure includes a manipulator having a distal end to which a surgical tool is attached, and an input device that operates the manipulator, in which the input device includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, a motor that rotates the base end of the follower link around the follower rotation axis, and a controller configured to perform feedback control of a rotation position of the follower link using a rotation position deviation of a rotation position of the second gimbal link with respect to the second reference rotation position as a rotation position deviation of the follower link by controlling an operation of the motor.

This configuration can prevent interference between the links configuring the gimbal of the wrist unit.

A controller according to still another aspect is configured to control an input device that operates a manipulator having a distal end to which a surgical tool is attached, in which the input device includes an arm unit having a joint, a wrist unit including a follower link having a base end rotatably connected to a distal end of the arm unit around a follower rotation axis, a first gimbal link having a base end rotatably connected to a distal end of the follower link around a first gimbal rotation axis orthogonal to the follower rotation axis, a second gimbal link having a base end rotatably connected to a distal end of the first gimbal link around a second gimbal rotation axis that is orthogonal to the first gimbal rotation axis and coincides with the follower rotation axis when the first gimbal link is located at a first reference rotation position, and an operation unit as a third gimbal link having a base end rotatably connected to a distal end of the second gimbal link around a third gimbal rotation axis that is orthogonal to the second gimbal rotation axis and is orthogonal to the first gimbal rotation axis when the second gimbal link is located at a second reference rotation position, and a motor that rotates the base end of the follower link around the follower rotation axis, and the controller is configured to perform feedback control of a rotation position of the follower link using a rotation position deviation of a rotation position of the second gimbal link with respect to the second reference rotation position as a rotation position deviation of the follower link by controlling an operation of the motor.

This configuration can prevent interference between the links configuring the gimbal of the wrist unit.

Embodiments of the present invention will now be described with reference to the drawings. In the following description, the same or corresponding elements are denoted by the same reference signs throughout all the drawings, and redundant description thereof is omitted. The following drawings are for describing the present disclosure, and therefore, in some cases, elements irrelevant to the present disclosure may be omitted in the drawings, dimensions may not be accurate due to exaggeration or the like, or the corresponding elements in the drawings may not match.

Hereinafter, the "rotation position" refers to the "rotation angle". The "rotation position" is used when a use of a concept of "position" facilitates understanding, and the "rotation angle" is used when a use of a concept of "angle" facilitates understanding. Further, the "rotation speed" refers to the "rotation angle speed". The "rotation speed" is used when a use of a concept of "speed" facilitates understanding, and the "rotation angle speed" is used when a use of a concept of "angle" facilitates understanding.

Further, the present disclosure is not limited to the following embodiments.

Embodiment

[Configuration]
{Configuration of Hardware}

FIG. 1 is a schematic diagram showing an outline of an example of a robot-assisted surgical system including an input device of a surgical manipulator according to an embodiment of the present disclosure. FIG. 2 is a schematic diagram showing an outline of an appearance of an example of a hand control included in the robot-assisted surgical system in FIG. 1. Hereinafter, a vertical direction in FIGS. 1 and 2 will be described as a vertical direction in an absolute space.

Referring to FIGS. 1 and 2, a robot-assisted surgical (RAS) system 200 includes a positioner 201, a surgical manipulator 202, and a hand control 100.

<Robot-Assisted Surgical System 200>

Referring to FIG. 1, for example, an operating table 203 is disposed in an operating room, and a patient 204 is laid on the operating table 203. The positioner 201 is disposed near the operating table 203. The positioner 201 is configured by, for example, an articulated robot. The surgical manipulator 202 configured by the articulated robot is attached to a base 201a which is a distal end of the positioner 201. The surgical manipulator 202 has, for example, a base part, an arm unit 401, and an end effector. The base part is fixed to the base 201a. The base part and links 404, the links 404, and the links 404 and the end effector are connected by a plurality of joints. A plurality of (here, for example, four) the arm units 401 is connected to the base part. A surgical tool 402 is attached to a distal end of each of the plurality of arm units 401 as an end effector.

The positioner 201 transports the surgical manipulator 202 to a position where the surgical manipulator 202 is suitable for performing an operation on the patient 204.

<Hand Control 100>

FIG. 2 is an outline of the hand control 100. FIG. 2 is a diagram to help understand a concept of the hand control 100. Thus, FIG. 2 shows, in particular, a detailed structure of the input device 2 differently from a specific structure of the input device 2 to be described later, shown in FIGS. 3 to 6.

Referring to FIG. 2, the hand control 100 is a device with which an operator (a doctor who performs a surgical operation) controls an operation of the surgical manipulator 202 to perform a surgical operation. The hand control 100 is electrically connected to the positioner 201 and the surgical manipulator 202 by wire or wirelessly. The hand control 100 is disposed, for example, near the operating table or in a separate room.

Here, the hand control 100 includes a body 1, the input device 2, a plurality of pedals 4, a display unit 5, and a viewer (not shown).

The body 1 has a substantially L shape as viewed from a side. A right input device 2A and a left input device 2B (input device of the surgical manipulator) are provided on a right side and a left side of the body 1, respectively, as facing to the body 1. The right input device 2A and the left input device 2B are used for the operator to operate with the right and left hands, respectively. The right input device 2A and the left input device 2B function as master input devices for the arm units 401 of the surgical manipulator 202 as a slave robot.

A U-shaped support member 3 is provided at an upper part of the body 1 so as to protrude forward. The display unit 5 is provided at a center of a front end of the support member 3. The display unit 5 is configured by, for example, a touch panel, and functions as a screen on which the operator displays or inputs information for performing various settings on the hand control 100. The viewer (not shown) is provided at an upper part of the hand control 100. However, because a configuration and a function of the viewer are well known, the viewer is not shown in FIG. 2 to make the input device 2 easy to see. The viewer displays an image captured by an endoscope (surgical tool 402) attached as the end effector to the distal end of one of the arm units 401 of the surgical manipulator 202.

The plurality of (four, here) pedals 4 are provided at a lower part of the body 1 so as to protrude forward. The plurality of pedals 4 switches a connection between the right input device 2A and the left input device 2B and the arms of the surgical manipulator 202, zooms an image displayed on a display unit 5, and the like.

The operator, for example, operates the right input device 2A or the left input device 2B with the right hand or the left hand, respectively, to perform an operation while sitting on a chair disposed in front of the hand control 100, and viewing an image of the body of the patient 204 displayed on the viewer.

<Input Device 2 of Surgical Manipulator 202>

FIG. 3 is a side view schematically showing an outline of the input device 2 shown in FIG. 2. FIG. 3 shows a simplified configuration of the input device 2. Refer to FIGS. 4 to 6 for an example of a specific structure of the input device 2. FIG. 3 shows a right input device 2A. A left input device 2B has a structure in which a lateral direction is simply in reverse to a lateral direction of the structure of the right input device 2A. Therefore, a description of the left input device 2B is omitted. Hereinafter, for convenience, the vertical direction and the lateral direction in FIG. 3 are the vertical direction and a front and rear direction of the right input device 2A, respectively. The right input device 2A takes a reference posture shown in FIG. 3 in an initial state.

Referring to FIG. 3, the right input device 2A takes a reference posture having an elbow-shaped (L-shaped) as viewed from a side. Hereinafter, the reference posture of the right input device 2A may be simply referred to as "reference posture". The right input device 2A includes a master arm 10. The master arm 10 includes an arm unit 11 and a wrist unit 12.

{Arm Unit 11}

The arm unit 11 includes, for example, a base body 21, a first link 22, a second link 23, and a third link 24. The base body 21 is fixed to the body 1 of the hand control 100. One end (here, upper end) of the first link 22 is connected via a first joint JT1 to one end (here, lower end) of the base body 21 in the vertical direction rotatably around a first rotation axis A1 extending in the vertical direction. One end (here, upper end) of the second link 23 is connected via a second joint JT2 to the other end (here, lower end) of the first link 22 rotatably around a second rotation axis A2 orthogonal to the first rotation axis A1 and extending in the lateral direction. One end (rear end in the reference posture) of the third link 24 is connected via a third joint JT3 to the other end (here, lower end) of the second link 23 rotatably around a third rotation axis A3 extending in parallel to the second rotation axis A2. One end of a swing member 25 is provided at the other end of the first link 22 rotatably around the second rotation axis A2. One end (here, upper end) of an auxiliary link 26 is connected to the other end of the swing member 25 rotatably around a ninth rotation axis A9. The ninth rotation axis A9 extends in parallel to the second rotation axis A2 and apart from the second rotation axis by a predetermined distance. The other end (here, lower end) of the auxiliary link 26 is connected to one end of the third link 24 rotatably around a tenth rotation axis A10. The tenth rotation axis A10 extends in a direction parallel to the third rotation axis A3 and toward the one end of the third link 24 from the third rotation axis apart from the third rotation axis by the predetermined distance. That is, the auxiliary link 26 and the second link 23 configure parallel links.

The wrist unit 12 is connected via a fourth joint JT4 to the other end (front end in the reference posture) of the third link 24 rotatably around a follower rotation axis (fourth rotation axis) A4. The follower rotation axis A4 extends so as to be orthogonal to a plane including the third rotation axis A3 and the tenth rotation axis A10.

A shoulder unit is configured by the base body 21, which has a frame shape. The base body 21 is provided with a first motor M1 (see FIG. 7) facing downward. Specifically, the first motor M1 is provided such that a main shaft (not shown) is coaxial with the first rotation axis A1. The first motor M1 is provided with a first rotation angle detector E1 (see FIG. 7) that detects a rotation angle of the first motor M1. The first rotation angle detector E1 only has to be able to detect the rotation angle, and is configured by, for example, an encoder or a tachometer. Here, the first rotation angle detector E1 is configured by an encoder directly connected to the main shaft of the first motor M1. The main shaft of the first motor M1 is coaxially butted and connected to a first rotation shaft (not shown) of the first link 22 by using a cylindrical connection member (not shown).

An upper arm unit of the arm unit 11 includes the first link 22, the second link 23, and the auxiliary link 26. The first link 22 has a frame shape. The first rotation shaft is provided at the one end (here, upper end) of the first link 22. As described above, the first rotation shaft is coaxially connected to the main shaft of the first motor M1. The first joint JT1 is configured by the first rotation shaft and the first motor M1. As a result, the first link 22 can freely rotate around the first rotation axis A1 with respect to the base body 21. The rotation angle of the first motor M1 created by the rotation of the first link 22 can be detected by the first rotation angle detector E1. The first motor M1 can drive the first rotation shaft to rotate.

The second link has a hollow rod shape. A second rotation shaft (not shown) is provided at the one end (upper end) of the second link 23. The second rotation shaft is attached to the other end (lower end) of the first link 22 via a bearing (not shown) rotatably around the second rotation axis A2. The second rotation shaft and the bearing configure the second joint JT2, whereby the second link 23 can freely rotate around the second rotation axis A2 with respect to the first link 22.

A driven pulley (not shown) is provided on the second rotation shaft. Meanwhile, the first link 22 is provided with a second motor M2 (see FIG. 7) such that a central axis of a main shaft is parallel to the second rotation axis A2. The second motor M2 is provided with a second rotation angle detector E2 (see FIG. 7) that detects a rotation angle of the second motor M2. The second rotation angle detector E2 only has to be able to detect the rotation angle, and is configured by, for example, an encoder or a tachometer. Here, the second rotation angle detector E2 is configured by an encoder directly connected to the main shaft (not shown) of the second motor M2.

The main shaft of the second motor M2 is provided with a drive pulley (not shown). A belt (not shown) is wound around the drive pulley and the driven pulley (not shown). Therefore, the rotation angle of the second motor M2 created by the rotation of the second link 23 can be detected by the second rotation angle detector E2, and the second motor M2 can drive the second rotation shaft to rotate.

Further, a tension coil spring (not shown) is provided between an appropriate position (here, center) of the second link 23 and the first link 22. The tension coil spring is provided such that a central axis of the tension coil spring is orthogonal to the second rotation axis A2 and the third rotation axis A3. Further, the tension coil spring is designed such that a predetermined torque acts on the second rotation shaft in a rotation direction of the second link 23 when the second link 23 rotates from the reference posture. This predetermined torque is set so as to cancel a part of a torque generated on the second rotation shaft by a weight of a part of the arm unit 11 from the second link 23 ahead and a weight of the wrist unit 12 (hereinafter, the torque may be referred to as a gravity torque). As a result, a part of the gravity torque generated on the second rotation shaft is canceled by the tension coil spring.

The third link 24 is a rod-shaped box, and houses main elements therein. A third rotation shaft (not shown) is provided at the one end (rear end) of the third link 24. The third rotation shaft is attached to the other end of the second link 23 via a bearing (not shown) rotatably around the third rotation axis A3. The third rotation shaft and the bearing configure the third joint JT3, whereby the third link 24 can freely rotate around the third rotation axis A3 with respect to the second link 23.

Meanwhile, the swing member 25 has an elongated plate shape, and an eleventh rotation shaft (not shown) is provided at one end of the swing member 25. The eleventh rotation shaft is attached to the other end of the first link 22 via a bearing (not shown) rotatably around the second rotation axis A2.

A ninth rotation shaft (not shown) is provided at the other end of the swing member 25. The ninth rotation shaft is connected via a bearing (not shown) to the one end (here, upper end) of the auxiliary link 26 rotatably around the ninth rotation axis A9.

Further, a tenth rotation shaft (not shown) is provided at a part between the one end of the third link 24 and the third joint JT3. The tenth rotation shaft is connected via a bearing (not shown) to the other end (here, lower end) of the auxiliary link 26 rotatably around the tenth rotation axis A10. As described above, the auxiliary link 26 and the second link 23 configure parallel links.

Further, a driven pulley (not shown) is provided on the eleventh rotation shaft (not shown). Meanwhile, a third motor M3 (see FIG. 7) is provided at an appropriate position of the first link 22 such that a central axis of a main shaft (not shown) is parallel to an eleventh rotation axis A11. The third motor M3 is provided with a third rotation angle detector E3 (see FIG. 7) that detects a rotation angle of the third motor M3. The third rotation angle detector E3 only has to be able to detect the rotation angle, and is configured by, for example, an encoder or a tachometer. Here, the third rotation angle detector E3 is configured by an encoder directly connected to the main shaft of the third motor M3.

The main shaft of the third motor M3 is provided with a drive pulley (not shown). A belt (not shown) is wound around the drive pulley and the driven pulley.

With the above configuration of the auxiliary link 26, when the third link 24 rotates, the auxiliary link 26 moves in parallel to the second link 23, whereby the swing member 25 swings, and the driven pulley, the drive pulley, and the third motor M3 rotate in that order in accordance with the swing of the swing member 25. Therefore, by this series of operations, the rotation angle of the third motor M3 created by the rotation of the third link 24 can be detected by the third rotation angle detector E3. Further, the third motor M3 can drive the third rotation shaft to rotate by an operation reverse to this series of operations.

Further, a compression coil spring (not shown) is provided between the swing member 25 and the first link 22. The compression coil spring is designed to always generate a torque that rotates the swing member downward. This torque is set so as to cancel a part of the gravity torque generated on the ninth rotation shaft by a weight of the third link 24 of the arm unit 11 and the weight of the wrist unit 12. As a result, a part of the gravity torque generated on the ninth rotation shaft is canceled by the coil spring.

{Wrist Unit 12}

FIG. 4 is a perspective view showing an appearance of the wrist unit 12 of the input device in FIG. 3. FIG. 4 shows the wrist unit 12 in the reference posture. Referring to FIG. 4, the wrist unit 12 includes, for example, a follower link (fourth link) 71, a first gimbal link (fifth link) 72, a second gimbal link (sixth link) 73, and an operation unit 74 as a third gimbal link (seventh link). The follower link 71, the first gimbal link 72, the second gimbal link 73, and the operation unit 74 configure a gimbal having three axes (three degrees of freedom).

Specifically, a base end of the follower link 71 is rotatable around the follower rotation axis A4 with respect to a distal end of the third link 24, a base end of the first gimbal link 72 is rotatable around a first gimbal rotation axis (fifth rotation axis) A5 with respect to a distal end of the follower link 71, a base end of the second gimbal link 73 is rotatable around a second gimbal rotation axis (sixth rotation axis) A6 orthogonal to the first gimbal rotation axis A5 with respect to a distal end of the first gimbal link 72, and the operation unit 74 is rotatable around a third gimbal rotation axis (seventh rotation axis) A7 orthogonal to the second gimbal rotation axis A6 with respect to a distal end of the second gimbal link 73.

In the wrist unit 12 in the reference posture, the first gimbal link 72 is in the first reference rotation position. In this case, the second gimbal rotation axis A6 coincides with the follower rotation axis (fourth rotation axis) A4. In the wrist unit 12 in the reference posture, the second gimbal link 73 is in the second reference rotation position. In this case, the third gimbal rotation axis A7 is orthogonal to the first gimbal rotation axis A5.

Therefore, the operator can rotate the operation unit 74 around an intersection of these three rotation axes A5 to A7 as a center to direct the operation unit 74 in any direction.

Referring to FIGS. 3 and 4, the follower link 71 has an elbow shape (L shape), and one end (front end in the reference posture) of the follower link 71 is connected via the fourth joint JT4 to the other end (front end in the reference posture) of the third link 24 (see FIG. 3) rotatably around the follower rotation axis A4. The follower rotation axis A4 is orthogonal to the plane including the third rotation axis A3 and the tenth rotation axis A10.

Referring to FIG. 4, one end (rear end in the reference posture) of the first gimbal link 72 is connected via a fifth joint JT5 to the other end (rear end in the reference posture) of the follower link 71 rotatably around the first gimbal rotation axis A5 orthogonal to the follower rotation axis A4. The first gimbal link 72 has an elbow shape (L shape) that is slightly smaller than the follower link 71. One end (right end in the reference posture) of the second gimbal link 73 is connected via a sixth joint JT6 to the other end (front end in the reference posture) of the first gimbal link 72 rotatably around the second gimbal rotation axis A6. The second gimbal link 73 has an elbow shape (L shape) that is slightly smaller than the first gimbal link 72. One end (left end in the reference posture) of the operation unit 74 is connected via a seventh joint JT7 to the other end (left end in the reference posture) of the second gimbal link 73 rotatably around the third gimbal rotation axis A7. The operation unit 74 includes a rod-shaped body and a pair of cylindrical finger insertion parts 74a provided on the body. The pair of finger insertion parts 74a is configured such that the operator can insert the thumb and the forefinger therein and operate the pair of finger insertion parts 74a as if pinching or releasing an object with the thumb and the forefinger.

Here, the follower link 71 extends on a plane including the follower rotation axis A4 and the first gimbal rotation axis A5 which are orthogonal to each other. The first gimbal link 72 extends on a plane A including the first gimbal rotation axis A5 and the second gimbal rotation axis A6 which is orthogonal to each other. The second gimbal link 73 extends on a plane B including the second gimbal rotation axis A6 and the third gimbal rotation axis A7 which are orthogonal to each other. In this case, when the second gimbal link 73 is located at the second reference rotation position, the plane B on which the second gimbal link 73 extends is orthogonal to the plane A on which the first gimbal link 72 extends. That is, an included angle between the second gimbal link 73 and the first gimbal link 72 is a right angle when viewed from an extending direction of the second gimbal rotation axis A6. Then, when the second gimbal link 73 rotates to near the first gimbal link 72 from this state, a lower end 73a of the second gimbal link 73 interferes with the first gimbal link 72.

Next, an example of a detailed structure of the wrist unit 12 will be described.

FIG. 5 is a sectional view showing a vertical section of the follower link 71 and the first gimbal link 72 of the wrist unit 12 in FIG. 4. FIG. 6 is a sectional view showing a vertical section of the second gimbal link 73 and the operation unit 74 of the wrist unit 12 in FIG. 4. FIG. 5 is a sectional view of the wrist unit 12 taken along the plane A including the first gimbal rotation axis A5 and the second gimbal rotation axis A6. FIG. 6 is a sectional view of the wrist unit 12 taken along the plane B including the second gimbal rotation axis A6 and the third gimbal rotation axis A7.

Referring to FIG. 5, the follower link 71 is an elbow-shaped (L-shaped) box, which houses main elements therein. A fourth rotation shaft R4 is provided at the one end (front end) of the follower link 71. The fourth rotation shaft R4 is attached to the other end (front end) of the third link 24 via a bearing 81 rotatably around the follower rotation axis A4. The fourth rotation shaft R4 and the bearing 81 configure the fourth joint JT4, whereby the follower link 71 can freely rotate around the follower rotation axis A4 with respect to the third link 24.

Further, a fourth motor M4 is provided inside the third link 24 such that a central axis of a main shaft S4 is orthogonal to the follower rotation axis A4. The fourth motor M4 is provided with a fourth rotation angle detector E4 that detects a rotation angle of the fourth motor M4. The fourth rotation angle detector E4 only has to be able to detect the rotation angle, and is configured by, for example, an encoder or a tachometer. Here, the fourth rotation angle detector E4 is configured by an encoder directly connected to the main shaft S4 of the fourth motor M4. The main shaft S4 of the fourth motor M4 is connected to the fourth rotation shaft R4 via a bevel gear mechanism G1. Therefore, the rotation angle of the fourth motor M4 created by the rotation of the follower link 71 can be detected by the fourth rotation angle detector E4, and the fourth motor M4 can drive the fourth rotation shaft R4 to rotate.

The first gimbal link 72 is an elbow-shaped (L-shaped) box, which houses main elements therein. A fifth rotation shaft R5 is provided at the one end (rear end) of the first gimbal link 72. The fifth rotation shaft R5 is attached to the other end (rear end) of the follower link 71 via a bearing 82 rotatably around the first gimbal rotation axis A5. The fifth rotation shaft R5 and the bearing 82 configure the fifth joint JT5, whereby the first gimbal link 72 can freely rotate around the first gimbal rotation axis A5 with respect to the follower link 71.

Further, a fifth motor M5 is provided inside the follower link 71 such that a central axis of a main shaft S5 is orthogonal to the first gimbal rotation axis A5. The fifth motor M5 is provided with a fifth rotation angle detector E5 that detects a rotation angle of the fifth motor M5. The fifth rotation angle detector E5 only has to be able to detect the rotation angle, and is configured by, for example, an encoder or a tachometer. Here, the fifth rotation angle detector E5 is configured by an encoder directly connected to the main shaft S5 of the fifth motor M5. The main shaft S5 of the fifth motor M5 is connected to the fifth rotation shaft R5 via a bevel gear mechanism G2. Therefore, the rotation angle of the fifth motor M5 created by the rotation of the first gimbal link 72 can be detected by the fifth rotation angle detector E5, and the fifth motor M5 can drive the fifth rotation shaft R5 to drive.

Further, a compression coil spring SP2 is provided between an appropriate position of the follower link 71 (here, the lower end of the rear end in the reference posture) and the fifth rotation shaft R5. The compression coil spring SP2 is provided such that a central axis of the compression coil spring SP2 is parallel to the follower rotation axis A4 and orthogonal to the first gimbal rotation axis A5. Further, the compression coil spring SP2 is designed such that when the first gimbal link 72 rotates from the reference posture, a predetermined torque acts on the first gimbal link 72 in the rotation direction. This predetermined torque is set so as to cancel a part of the gravity torque generated on the fifth rotation shaft R5 by a weight of a part of the wrist unit 12 from the first gimbal link ahead. As a result, a part of the gravity torque generated on the fifth rotation shaft R5 is canceled by the compression coil spring SP2.

Referring to FIGS. 5 and 6, the second gimbal link 73 is an elbow-shaped (L-shaped) box, which houses main elements therein. A sixth rotation shaft R6 is provided at the one end (right end) of the second gimbal link 73. The sixth rotation shaft R6 is attached to the other end (front end) of the first gimbal link 72 via a bearing 83 rotatably around the second gimbal rotation axis A6. The sixth rotation shaft R6 and the bearing 83 configure the sixth joint JT6, whereby the second gimbal link 73 can freely rotate around the second gimbal rotation axis A6 with respect to the first gimbal link 72.

Further, a sixth motor M6 is provided inside the first gimbal link 72 such that a central axis of a main shaft S6 is orthogonal to the second gimbal rotation axis A6. The sixth motor M6 is provided with a sixth rotation angle detector E6 that detects a rotation angle of the sixth motor M6. The sixth rotation angle detector E6 only has to be able to detect the rotation angle, and is configured by, for example, an encoder or a tachometer. Here, the sixth rotation angle detector E6 is configured by an encoder directly connected to the main shaft S6 of the sixth motor M6. The main shaft S6 of the sixth motor M6 is connected to the sixth rotation shaft R6 via a bevel gear mechanism G3. Therefore, the rotation angle of the sixth motor M6 created by the rotation of the second gimbal link 73 can be detected by the sixth rotation angle detector E6, and the sixth motor M6 can drive the sixth rotation shaft R6 to rotate.

Referring to FIG. 6, a seventh rotation shaft R7 is provided at the one end (left end) of the operation unit 74. The seventh rotation shaft R7 is attached to the other end (left end) of the second gimbal link 73 via a bearing 84 rotatably around the third gimbal rotation axis A7. The seventh rotation shaft R7 and the bearing 84 configure the seventh joint JT7, whereby the operation unit 74 can freely rotate around the third gimbal rotation axis A7 with respect to the second gimbal link 73.

Further, a seventh motor M7 is provided inside the second gimbal link 73 such that a central axis of a main shaft S7 is orthogonal to the third gimbal rotation axis A7. The seventh motor M7 is provided with a seventh rotation angle detector E7 that detects a rotation angle of the seventh motor M7. The seventh rotation angle detector E7 only has to be able to detect the rotation angle, and is configured by, for example, an encoder or a tachometer. Here, the seventh rotation angle detector E7 is configured by an encoder directly connected to the main shaft S7 of the seventh motor M7. The main shaft S7 of the seventh motor M7 is connected to the seventh rotation shaft R7 via a bevel gear mechanism G4. Therefore, the rotation angle of the seventh motor M7 created by the rotation of the operation unit 74 can be detected by the seventh rotation angle detector E7, and the seventh motor M7 can drive the seventh rotation shaft R7 to rotate.

{Configuration of Control System}

FIG. 7 is a functional block diagram showing an example of a configuration of a control system of the right input device 2A and the surgical manipulator 202.

Referring to FIG. 7, the right input device 2A includes an input device controller (input device control circuit) C1. The input device controller C1 is, for example, provided commonly in the right input device 2A and the left input device 2B. The input device controller C1 controls both of the input devices similarly, and thus here, only the control of the right input device 2A will be described, and a description of the control of the left input device 2B will be omitted. Note that an input device controller C1 may be provided in the right input device 2A and the left input device 2B, individually. A detailed configuration of the input device controller C1 will be described later. The input device controller C1 is provided, for example, at an appropriate position of the hand control 100.

In the right input device 2A, the first to seventh rotation angle detectors (first to seventh rotation angle sensors) E1 to E7 detect the rotation angles AG of the first to seventh motors M1 to M7 respectively corresponding to the first to seventh joints JT1 to JT7. The detected rotation angles AG of the first to seventh motors M1 to M7 are output to the input device controller C1. The input device controller C1 generates a position (position command signal) P of the operation unit 74 on the basis of the input rotation angles AG of the first to seventh motors M1 to M7, and outputs the position P of the operation unit 74 to a manipulator controller (manipulator control circuit) C2. Further, the input device controller C1 outputs a drive current CR to the first to seventh motors M1 to M7, respectively, on the basis of the input rotation angles AG of the first to seventh motors M1 to M7.

In the surgical manipulator 202, one or more rotation angle detectors E202 detect rotation angles of one or more motors M202 respectively corresponding to one or more joints that connect the links 404 and the surgical tool 402 of the arm unit 401, and output the one or more detected rotation angles of the motor M202 to the manipulator controller C2. On the basis of the position (position command signal) P of the operation unit 74 input from the input device controller C1, the manipulator controller C2 outputs to the one or more motors M202 the drive current such that the surgical tool 402 is located at a position corresponding to the position of the operation unit 74. An operation of the links 404 is thereby controlled such that the surgical tool 402 is located at a position corresponding to the position of the operation unit 74. At this time, the rotation angle detected by the one or more rotation angle detectors E202 is used to feedback control the position of the surgical tool 402.

Note that a posture and an operation of the operation unit 74 of the input device 2A are separately detected by an appropriate sensor (not shown), and are input to the manipulator controller C2 via the input device controller C1. The manipulator controller C2 controls the surgical tool 402 such that the surgical tool 402 takes a posture corresponding to the posture of the operation unit 74 of the input device 2A and performs an operation corresponding to the operation of the operation unit 74 of the input device 2A. The manipulator controller C2 is provided, for example, at an appropriate position of the hand control 100.

<Input Device Controller C1>

*Configuration of Gimbal Link Interference Prevention Control*

FIG. 8 is a functional block diagram showing an example of a configuration of gimbal link interference prevention control of the input device controller in FIG. 7.

Referring to FIG. 8, the configuration of the gimbal link interference prevention control includes a position control unit 501, an addition and subtraction unit 502, a speed control unit 503, an addition and subtraction unit 505, a servo amplifier (power converter) 506, a differentiation unit 507, an FF speed command generation unit 508, and a differentiation unit 509.

The position control unit 501, the addition and subtraction unit 502, the speed control unit 503, a gravity compensation unit 504, the addition and subtraction unit 505, the differentiation unit 507, the FF speed command generation unit 508, and the differentiation unit 509 are configured by, for example, an arithmetic unit (not shown) including a processor (not shown) and a memory (not shown). Examples of the arithmetic unit include a microcontroller. Examples of the processor include a CPU, an MPU, a field programmable gate array (FPGA), and a programmable logic controller (PLC). Examples of the memory include an internal memory of the processor such as ROM and RAM and an external memory such as a hard disk drive.

The position control unit 501, the addition and subtraction unit 502, the speed control unit 503, the gravity compensation unit 504, the addition and subtraction unit 505, the differentiation unit 507, the FF speed command generation unit 508, and the differentiation unit 509 are a functional block provided by the processor of the arithmetic unit reading and executing a predetermined control program stored in the memory of the arithmetic unit. Actually, the arithmetic unit operates as the position control unit 501, the addition and subtraction unit 502, the speed control unit 503, the gravity compensation unit 504, the addition and subtraction unit 505, the differentiation unit 507, the FF speed command generation unit 508, and the differentiation unit 509.

The position control unit 501, the addition and subtraction unit 502, the speed control unit 503, the gravity compensation unit 504, the addition and subtraction unit 505, the differentiation unit 507, the FF speed command generation unit 508, and the differentiation unit 509 may be configured by hardware such as an electronic circuit. The input device controller C1 may be configured by a single arithmetic unit or a plurality of arithmetic units.

In other words, the functions of the elements disclosed herein can be executed by using general purpose processors, special purpose processors, integrated circuits, application specific integrated circuits (ASICs), conventional circuits that are configured to perform the disclosed functions and/or a circuit or a processing circuit including a combination thereof. The processor, which includes transistors and other circuits, is considered as a processing circuit or a circuit. In the present disclosure, a circuit, a "device" or a "unit" is hardware that performs the recited function or is programmed to perform the recited function. The hardware may be the hardware disclosed herein or any other known hardware programmed or configured to perform the recited functions. When the hardware is a processor that is considered as a type of circuit, a circuit, a "device", or a "unit" is a combination of hardware and software, and the software is used to configure the hardware and/or the processor.

*Gravity Compensation*

First, a configuration of the gravity compensation will be described. The gravity compensation unit 504 obtains a posture of the master arm 10 on the basis of the input rotation angles AG of the first to seventh motors M1 to M7, and calculates a gravity canceling torque that cancels the gravity torque generated at the first to seventh rotation shafts of the first to seventh joints JT1 to JT7 by the posture. In this case, the gravity compensation unit 504 calculates the gravity torque determined for each of the first to seventh rotation shafts from the obtained postures. Then, in the joints JT2, JT3, and JT5 provided with the coil springs, the torque in the opposite direction to the torque obtained by subtracting the torque generated by the coil springs from the gravity torque is defined as the gravity canceling torque. In the joints JT1, JT4, JT6, and JT7 provided with no coil springs, the torque in the opposite direction to the gravity torque is defined as the gravity canceling torque. The gravity canceling torque of the first to seventh joints JT1 to JT7 is a gravity compensation amount. The gravity compensation unit 504 sends the gravity compensation amount of the first to seventh joints JT1 to JT7 as a gravity compensation current command Ig for performing gravity compensation of the gravity compensation amount.

*Gimbal Link Interference Prevention Control*

Next, the configuration of the gimbal link interference prevention control will be described. When the operation unit 74 is operated and the sixth joint JT6 rotates (the second gimbal link 73 rotates), the sixth motor M6 connected to the sixth joint JT6 via the power transmission mechanism rotates. The sixth rotation angle detector E6 detects this rotation and outputs a rotation angle AG6 that has been detected. The position control unit 501 calculates a deviation of the rotation angle AG6 from the second reference rotation position and converts the deviation to a speed command v1.

Meanwhile, the differentiation unit 509 differentiates the rotation angle AG6 from the sixth rotation angle detector E6 to generate a rotation angle speed vf6. The FF speed command generation unit 508 generates the speed command v2 for feedforward control on the basis of the rotation angle speed vf6.

Meanwhile, the fourth rotation angle detector E4 detects the rotation of the fourth motor M4 that drives the fourth joint (follower link 71), and outputs a rotation angle AG4 that has been detected. The differentiation unit 507 differentiates the rotation angle AG4 and outputs a feedback rotation angle speed vf4.

The addition and subtraction unit 502 adds the speed command v1 and the speed command v2 for feedforward control and subtracts the feedback rotation angle speed vf4 from the obtained value to generate a speed deviation ve. The speed control unit 503 generates a current command Ic on the basis of the speed deviation ve.

Meanwhile, a current sensor CS detects the drive current CR output by the servo amplifier 506 and outputs the detected drive current as a feedback current If. The addition and subtraction unit 505 adds the current command Ic and the gravity compensation current command Ig, and subtracts the feedback current If from the obtained value to generate a current deviation Ie. The servo amplifier 506 outputs the drive current CR to the fourth motor M4 on the basis of the current deviation Ie. The fourth motor M4 is operated by this drive current, and thereby drives the fourth joint JT4 and then the follower link 71.

As a result, the follower link 71 rotates to locate the second gimbal link 73 at the second reference rotation position. At this time, gravity compensation is performed for the follower link 71.

*Configuration of Position Control Unit 501*

Next, a configuration of the position control unit 501 will be described in detail. FIG. 9 is a block diagram showing a configuration of the position control unit 501 in FIG. 8.

Referring to FIG. 9, the position control unit 501 includes a subtraction unit 520, a reduction ratio correction unit 521, a primary filter 522, a dead zone 523, a first switch 524, a second switch 525, and a moving average unit 526.

The subtraction unit 520 subtracts a rotation angle AG6(0) of the second reference rotation position of the second gimbal link 73 from the rotation angle AG6 from the sixth rotation angle detector E6 to generate the rotation position deviation of the second gimbal link 73. Here, the rotation angle AG6(0) at the second reference rotation position is 0 degrees.

The reduction ratio correction unit 521 applies a reduction ratio correction to this rotation position deviation and converts the corrected rotation position deviation to a rotation position deviation corresponding to a reduction ratio of the fourth joint JT4. In the present embodiment, the reduction ratio of the sixth joint JT6 and the reduction ratio of the fourth joint JT4 are different. Thus, the rotation angle AG6 detected by the sixth rotation angle detector E6 when the second gimbal link 73 makes one rotation at the sixth joint JT6 and the fourth rotation angle AG4 detected by the fourth rotation angle detector E4 when the follower link 71 makes one rotation at the fourth joint JT4 are different in accordance with a ratio of a reverse ratio of the reduction ratio RR6 of the sixth joint JT6 (1/RR6) and a reverse ratio of the reduction ratio of the fourth joint JT4 (1/RR4), representing the reduction ratio of the six joint JT6 as RR6 and the reduction ratio of the fourth joint JT4 as RR4. In order to correct this difference, reduction ratio correction is applied to the rotation position deviation. Specifically, this rotation position deviation is multiplied by RR6/RR4.

Next, the primary filter 522 removes a high frequency component from this position deviation. The high frequency component differs for each input device 2, and thus a time constant of the primary filter 522 may be adjustable. In this case, for example, when a desired time constant is input to the input device controller C1 from an input unit (not shown), the input device controller C1 may be configured to change the time constant of the primary filter 522 to the input time constant.

Next, this position deviation is passed through the dead zone 523. The dead zone 523 prevents chattering when the position deviation is minute (when an operation of the second gimbal link 73 is minute). The position deviation that has passed through the dead zone 523 is passed through the first switch 524 and the second switch 525. The first switch 524 is turned on when an operating flag f1 is turned on, and the first switch 524 is turned off when the operating flag f1 is turned off. The second switch 525 is turned on when an operation range flag f2 is turned on, and the second switch 525 is turned off when the operation range flag f2 is turned off.

The operating flag f1 is a flag indicating that the operation unit 74 is in operation. When a difference between the current rotation position (the rotation position in the current sampling) and the previous rotation position of the second gimbal link 73 (the rotation position in the previous sampling) exceeds a predetermined change threshold (for example, 1.0 degree), it is determined that the operation is in progress. The reason for providing the operating flag f1 is as follows.

As described above, when the second gimbal link 73 is rotated by the operation of the operation unit 74, the follower link 71 is rotated to locate the second gimbal link 73 at the second reference rotation position. If a slight rotation position deviation of the second gimbal link 73 remains when the operation is stopped, the follower link 71 continues to rotate and gives the operator discomfort. Then, the operating flag f1 is provided to avoid such discomfort given to the operator with a configuration in which feedback control of the rotation position of the follower link 71 is performed when the operation unit 74 is in operation, and the feedback control of the rotation position of the follower link 71 is stopped to stop the follower link 71 when the operation of the operation unit 74 is stopped.

The operation range flag f2 is a flag indicating that the follower link 71 is within a predetermined operation range. In the present embodiment, the follower link 71 has a structural movable range. It is therefore necessary to give a following command not to exceed the movable range. In order to prevent the interference of the second gimbal link 73, a rotation range to be followed by the follower link 71 is set as the operation range. When the follower link 71 has no structural movable range, the operation range flag f2 may be provided as necessary. The operation range is appropriately determined on the basis of a specification of the input device 2 and the like.

The moving average unit 526 takes a moving average of the position deviation that has passed through the first switch 524 and the second switch 525. As a result, a discontinuity of the position deviation that occurs when the first switch 524 or the second switch 525 operates is turned into continuity. Multiplying this position deviation xe obtained from a calculation of a moving average by a predetermined gain generates the speed command v1.

\*Configuration of FF Speed Command Generation Unit 508\*

Next, a configuration of the FF speed command generation unit 508 will be described in detail. FIG. 10 is a block diagram showing the configuration of the FF speed command generation unit 58 in FIG. 8.

Referring to FIG. 10, the FF speed command generation unit 508 includes a dead zone unit 531, a third switch 532, a first multiplication unit 533, a primary filter 534, a second multiplication unit 535, and a reduction ratio correction unit 536, and a third multiplication unit 537.

The rotation angle speed (rotation speed of the second gimbal link 73) vf6 from the differentiation unit 509 is passed through the dead zone 531. The dead zone 531 invalidates the speed feedforward control when the rotation angle speed vf6 is significantly small, in other words, when the operation of the operation unit 74 is slow. The rotation angle speed vf6 that has passed through the dead zone 531 is passed through the third switch 532. The third switch 532 is turned on when the operation range flag f2 is turned on, and the third switch 532 is turned off when the operation range flag f2 is turned off.

The first multiplication unit 533 multiplies the rotation angle speed vf6 that has passed through the third switch 532 by the continuation coefficient. FIG. 12 is a graph showing a relationship between the rotation angle (position) of the follower link 71 and the continuation coefficient as a first adjustment coefficient of the input of the speed feedforward control to the position feedback control loop. In FIG. 12, a horizontal axis represents the rotation angle (position) of the follower link 71, and a vertical axis represents the continuation coefficient.

Referring to FIG. 12, the continuation coefficient takes a value from 0 to 1.0. The continuation coefficient, for example, increases from 0 to 1.0 as the rotation angle of the follower link 71 near the operation lower limit of the follower link 71 increases from an operation lower limit. The continuation coefficient takes a value of 1.0 while the rotation angle of the follower link 71 increases to near an operation upper limit. The continuation coefficient decreases from 1.0 to 0 as the rotation angle of the follower link 71 increases from near the operation upper limit up to the operation upper limit. Note that, FIG. 12 shows that the continuation coefficient changes linearly near the operation lower limit and near the operation upper limit of the follower link 71. However, the continuation coefficient only has to monotonically change and may change in a curve.

The rotation angle (rotation position) AG4 of the follower link 71 detected by the fourth rotation angle detector E4 of the fourth joint JT4 is input to the first multiplication unit 533. The first multiplication unit 533 determines the continuation coefficient on the basis of the rotation angle AG4. The first multiplication unit 533 multiplies the rotation angle speed vf6 that has passed through the third switch 532 by the determined continuation coefficient.

Thus, when the follower link 71 enters the operation range from outside the operation lower limit and the third switch 532 is turned on, the rotation angle speed vf6 increases from 0 to an original value. Further, when the follower link 71 enters from outside the operation upper limit to inside the operation range and the third switch 532 is turned on, the rotation angle speed vf6 increases from 0 to the original value. That is, when the follower link 71 rotates from the outside to the inside of the operation range, the input of the speed feedforward control to the position feedback control loop is made continuous. This can prevent a sudden change in an addition amount of the rotation speed of the second gimbal link 73 by the feedforward control (input of the speed feedforward control to the position feedback control loop) when the follower link 71 rotates from the outside to the inside of the operation range, which gives the operator discomfort in the operation.

The primary filter 534 removes a high frequency component from the rotation angle speed vf6 multiplied by the continuation coefficient. The high frequency component differs for each input device 2, and thus the time constant of the primary filter 534 may be adjustable. In this case, for example, when a desired time constant is input to the input device controller C1 from an input unit (not shown), the input device controller C1 may be configured to change the time constant of the primary filter 534 to the input time constant.

Next, the second multiplication unit 535 multiplies the rotation angle speed vf6 by the FF adjustment coefficient. FIG. 13 is a graph showing a relationship between a rotation angle of the first gimbal link 72 and an FF adjustment coefficient as a second adjustment coefficient of the input of the speed feedforward control to the position feedback control loop. In FIG. 13, a horizontal axis represents the rotation angle (rotation position) of the first gimbal link 72, and a vertical axis represents the FF adjustment coefficient.

Referring to FIGS. 4 and 13, in the rotation of the first gimbal link 72, a minimum rotation angle, a maximum rotation angle, and +90 degrees are defined in a clockwise direction with the second reference rotation position as 0 degrees, and a negative minimum rotation angle, a negative maximum rotation angle, and −90 degrees are defined in a counterclockwise direction. The FF adjustment coefficient takes a value from 0 to 1.0. The FF adjustment coefficient takes a value of 1.0 while the first gimbal link 72 rotates clockwise to the minimum rotation angle. The FF adjustment coefficient linearly decreases to the minimum coefficient (for example, to 0.33) as the first gimbal link 72 rotates from the minimum rotation angle to the maximum rotation angle. The FF adjustment coefficient takes a value of the minimum coefficient while the first gimbal link 72 rotates from the maximum rotation angle to near +90 degrees. The FF adjustment coefficient linearly decreases from the minimum coefficient to 0 as the first gimbal link 72 rotates from near +90 degrees up to +90 degrees. Further, the FF adjustment coefficient takes a value of 1.0 while the first gimbal link 72 rotates counterclockwise to the negative minimum rotation angle. The FF adjustment coefficient linearly decreases to the minimum coefficient as the first gimbal link 72 rotates from the negative minimum rotation angle to the-maximum rotation angle. The FF adjustment coefficient takes a value of the minimum coefficient while the first gimbal link 72 rotates from the negative maximum rotation angle to near −90 degrees. The FF adjustment coefficient linearly decreases from the minimum coefficient to 0 as the first gimbal link 72 rotates from near −90 degrees up to −90 degrees. When an absolute value of the rotation angle of the first gimbal link 72 is 90 degrees or more, the follower link 71 rotates in a direction opposite to a direction in which the interference of the second gimbal link 73 is avoided. Thus, the FF adjustment coefficient is set to 0 when the absolute value of the rotation angle of the first gimbal link 72 is 90 degrees or more. The minimum coefficient, the minimum rotation angle, and the maximum rotation angle are parameters, and can be adjusted via the input unit (not shown) of the input device controller C1. Note that the changes in the FF adjustment coefficient in FIG. 13 are an example, and the changes in the FF adjustment coefficient with respect to the rotation position (rotation angle) of the first gimbal link 72 are not limited thereto. The FF adjustment coefficient only has to change so as to monotonically increasing from 0 and then monotonically decrease to 0 while the rotation position (rotation angle) of the first gimbal link 72 changes from −90° to +90°.

A rotation angle (rotation position) AG5 of the first gimbal link 72 detected by the fifth rotation angle detector E5 of the fifth joint JT5 is input to the second multiplication unit 535. The first multiplication unit 533 determines the FF adjustment coefficient on the basis of the rotation angle AG5. The determined FF adjustment coefficient is multiplied by the rotation angle speed vf6 that has passed through the primary filter 534.

When the rotation angle of the first gimbal link 72 from the first reference rotation position increases due to the operation of the operation unit 74, a rotation amount of the follower link 71 around the follower rotation axis A4 accompanying the rotation of the second gimbal link 73 from the second reference rotation position increases. When the rotation speed of the follower link 71 is high at that time, the operator feels discomfort in the operation.

This will be described in detail. FIG. 14 is a perspective view showing a state of the wrist unit 12 when the first gimbal link 72 rotates +45° from the first reference rotation position. FIG. 15 is a perspective view showing a state of the wrist unit 12 when the first gimbal link 72 rotates +90° from the first reference rotation position. In FIGS. 14 and 15, a reference numeral PR6 indicates a plane parallel to a rotation plane of the second gimbal link 73, and a reference numeral PR4 indicates a plane parallel to a rotation plane of the follower link 71.

First, referring to FIG. 4, in the reference posture of the wrist unit 12, the first gimbal link 72 is in the first reference rotation position. In this state, the second gimbal rotation axis A6 as the rotation axis of the second gimbal link 73 coincides with the follower rotation axis A4 as the rotation axis of the follower link 71. Therefore, when the second gimbal link 73 is rotated by the rotation angle θ from the second reference rotation position by the operation of the operation unit 74, the follower link 71 rotates in the same direction as the direction of this rotation by the same rotation angle as the angle θ.

Next, referring to FIG. 14, in a state of the wrist unit 12 in FIG. 14, the first gimbal link 72 is at the rotation position where the first gimbal link 72 rotates +45° from the first reference rotation position. In this state, the second gimbal rotation axis A6 is inclined by 45° with respect to the follower rotation axis A4. Thus, the rotation plane (plane parallel to the plane PR6) of the second gimbal link 73 is inclined by 45° with respect to the rotation plane of the follower link 71 (plane parallel to the plane PR4). Therefore, when the second gimbal link 73 is rotated by the rotation angle θ from the second reference rotation position by the operation of the operation unit 74, the follower link 71 is rotated on the rotation plane inclined by 45° with respect to the rotation plane by a rotation angle of the rotation angle θ or more.

Next, referring to FIG. 15, in a state of the wrist unit 12 in FIG. 15, the first gimbal link 72 is at the rotation position where the first gimbal link 72 rotates +90° from the first reference rotation position. In this state, the second gimbal rotation axis A6 is inclined by 90° with respect to the follower rotation axis A4. Thus, the rotation plane (plane parallel to the plane PR6) of the second gimbal link 73 is inclined by 90° with respect to the rotation plane of the follower link 71 (plane parallel to the plane PR4). Therefore, when the second gimbal link 73 is rotated by the rotation angle θ from the second reference rotation position by the operation of the operation unit 74, the follower link 71 is rotated on the rotation plane inclined by 90° with respect to the rotation plane to a rotation angle considerably larger than the rotation angle θ.

At that time, when the rotation speed of the follower link 71 is high, the operator feels discomfort in the operation.

In the second multiplication unit 535, when the rotation angle of the first gimbal link 72 from the first reference rotation position increases due to the operation of the operation unit 74, the rotation angle speed of the follower link 71 around the follower rotation axis A4 is suppressed, thereby preventing the operator from feeling discomfort in the operation.

The reduction ratio correction unit 536 corrects the rotation angle speed vf6 multiplied by the FF adjustment coefficient into a rotation angle speed corresponding to the reduction ratio of the fourth joint JT4 (RR4). This reduction ratio correction is similar to that of the above reduction ratio correction unit 521.

The third multiplication unit 537 multiplies the converted rotation angle by a predetermined gain to generate the speed command v2 for feedforward control.

[Operation]

First, the operations of the right input device 2A and the surgical manipulator 202 will be described.

Referring to FIGS. 3 and 4, the operator inserts, for example, the thumb and the forefinger into the pair of finger insertion parts 74a of the operation unit 74 of the right input device 2A. Then, when the operator moves the operation unit 74 left and right, the arm unit 11 rotates left and right around the first rotation axis A1 of the first joint JT1. When the operator moves the operation unit 74 back and forth, the arm unit 11 rotates back and forth around the second rotation axis A2 of the second joint JT2. When the operator moves the operation unit 74 up and down, the arm unit 11 rotates up and down around the third rotation axis A3 of the third joint JT3. When the operator rotates the wrist unit 12 left and right, the wrist unit 12 rotates left and right around the follower rotation axis A4 of the fourth joint JT4. When the operator operates the operation unit 74 to change a direction (posture) of the operation unit 74, the operation unit 74 moves (takes a posture) in a direction to be changed. Therefore, the operator can operate the input device 2A as intended.

When the operation unit 74 of the right input device 2A is operated, this operation is converted into a position command signal P by the input device controller C1. The manipulator controller C2 controls the operation of a selected one of the arm units 401 in accordance with this position command signal P such that the surgical tool 402 of the selected arm unit 401 of the surgical manipulator 202 is located at a position corresponding to the operation unit 74. Thus, the selected arm unit 401 of the surgical manipulator 202 operates in accordance with the operation of the right input device 2A by the operator. The arm unit 401 is selected by operating the pedals 4 of the hand control 100. An operation of the left input device 2B is similar to this operation.

Next, the gimbal link interference prevention control will be described. This control is performed by the processor described above reading and executing the control program stored in the memory. FIG. 11 is a flowchart showing the gimbal link interference prevention control. Hereinafter, a case where the operation unit 74 is operated in the reference posture of the wrist unit 12 shown in FIG. 4 will be described.

Referring to FIG. 11, the input device controller C1 first determines whether the rotation position deviation of the second gimbal link 73 is larger than a rotation deviation threshold value (step S1). This rotation deviation threshold value is set to 1.0 degree, for example. The dead zone 523 of the position control unit 501 operates in response to results of step S1.

When the rotation position deviation of the second gimbal link 73 is not larger than the rotation deviation threshold value (NO in step S1), the operating flag f1 and the operation range flag f2 are turned off (steps S9 and 10), and the first switch 524 and the second switch 525 of the position control unit 501 and the third switch 532 of the FF speed command generation unit 508 are turned off, and this control ends.

Meanwhile, when the rotation position deviation of the second gimbal link 73 is equal to or larger than the rotation deviation threshold value (YES in step S1), the input device controller C1 determines whether a rotation position change of the second gimbal link 73 is larger than the change threshold (step S2). The rotation position change is a difference between the current rotation position and the previous rotation position of the second gimbal link 73.

When the rotation position change of the second gimbal link 73 is not larger than the change threshold, the input device controller C1 starts counting in a counter (step S7). Then, it is determined whether a count value exceeds a threshold value (for example, 1,000 ms) (step S8). This counting is stopped when the rotation position change of the second gimbal link 73 exceeds the change threshold (step S4). When the count value does not exceed the threshold value (NO in step S8), it is determined that the operation has been performed within 1 second (1,000 ms) and the operation is performed, and the process returns to step S2. On the other hand, when the count value is equal to or more than the threshold value (YES in step S8), it is determined that the operation has been stopped for 1 second or more and the operation is stopped, the operating flag f1 and the operation range flag f2 are turned off (steps S9 and 10), and this control ends.

In step S2, when the rotation position change of the second gimbal link 73 is larger than the change threshold (YES in step S2), the input device controller C1 determines that the operation is in progress, turns on the operating flag f1 (step S3), and sets the count value of the counter to 0 (step S4). As a result, the first switch 524 of the position control unit 501 is turned on.

Next, the input device controller C1 determines whether the follower link 71 is in the operation range (step S5). When the follower link 71 is not in the operation range (NO in step S5), the operation range flag f2 is turned off (step S10), and this control ends.

On the other hand, when the follower link 71 is in the operation range (YES in step S5), the input device controller C1 turns on the operation range flag f2 (step S6).

Thus, the second switch 525 of the position control unit 501 and the third switch 532 of the FF speed command generation unit 508 are turned on, and the position feedback control and the feedforward control are performed. As a result, even if the second gimbal link 73 is rotated toward the first gimbal link 72 by the operation of the operation unit 74, the rotation of the follower link 71 causes the first gimbal link 72 to escape such that the included angle between the second gimbal link 73 and the first gimbal link 72 becomes a right angle, thereby preventing the second gimbal link 73 from interfering with the first gimbal link 72.

Further, even if the second gimbal link 73 is operated at a high speed by operating the operation unit 74, the follower link 71 follows quickly to prevent interference between the second gimbal link 73 and the first gimbal link 72.

The same applies to a case where the first gimbal link 71 of the wrist unit 12 is rotated from the first reference rotation position as shown in FIG. 14 or 15, except that the rotation amount of the follower link 71 may be large and the rotation speed of the follower link 71 may be suppressed at that time.

Further, gravity compensation is performed for each of the joints JT1 to JT7.

OTHER EMBODIMENTS

In the above embodiment, the gravity compensation unit 504 may be omitted.

From the above description, many modifications and other embodiments are apparent to a person skilled in the art. Therefore, the above description should be construed as illustrative only.

INDUSTRIAL APPLICABILITY

The input device for the surgical manipulator of the present disclosure, the robot-assisted surgical system including the input device, and the controller of the input device are useful as an input device of a surgical manipulator capable of preventing interference between links configuring a gimbal of a wrist unit, a robot-assisted surgical system including the input device, and a controller for the input device.

DESCRIPTION OF THE REFERENCE NUMERALS 1 body
2 input device
2A right input device
2B left input device
3 support member
4 pedal
5 display unit
10 master arm
11 arm unit
12 wrist unit
21 base body
22 first link
23 second link
24 third link
25 swing member
26 auxiliary link
71 follower link
72 first gimbal link
73 second gimbal link
74 operation unit
74a finger insertion part
81~82 bearing
100 hand control
200 robot-assisted surgical system
201 positioner
202 surgical manipulator
203 operating table
204 patient
401 arm unit
402 surgical tool 404 link
501 position control unit
504 gravity compensation unit
508 gravity compensation unit
A1 to A3 first rotation axis~third rotation axis
A4 follower rotation axis
A5 to A7 first gimbal rotation axis~third gimbal rotation axis
AG rotation angle
CR drive current
E1 to E7 first rotation angle detector~seventh rotation angle detector
G1 to G4 bevel gear mechanism
JT1 to JT7 first joint~seventh joint
M1 to M7 first motor~seventh motor
P position of the operation unit

What is claimed is:

1. An input device of a surgical manipulator, the input device comprising:
   an arm unit having a joint;
   a wrist unit including a follower link having a base end rotatably connected to a distal end of the arm unit around a follower rotation axis, a first gimbal link having a base end rotatably connected to a distal end of the follower link and rotatable with respect to a first reference rotation position around a first gimbal rotation axis orthogonal to the follower rotation axis, a second gimbal link having a base end rotatably connected to a distal end of the first gimbal link and rotatable with respect to a second reference rotation position around a second gimbal rotation axis that is orthogonal to the first gimbal rotation axis, the first reference rotation position of the first gimbal link corresponding to a position in which the second gimbal rotation axis coincides with the follower rotation axis, and an operation unit as a third gimbal link having a base end rotatably connected to a distal end of the second gimbal link around a third gimbal rotation axis that is orthogonal to the second gimbal rotation axis, the second reference rotation position of the second gimbal link corresponding to a position in which the third gimbal axis is orthogonal to the first gimbal rotation axis;
   a motor that rotates the base end of the follower link around the follower rotation axis; and
   a controller configured to perform interference prevention control of a rotation position of the follower link to maintain a second rotation position of the second gimbal link using a rotation position deviation between a rotation position of the second gimbal link and the second reference rotation position as a rotation position deviation of the follower link by controlling an operation of the motor, wherein
   the interference prevention control is performed only when the operation unit is operated to maintain the second rotation position by maintaining orthogonality between the first gimbal rotation axis and the third gimbal rotation axis to prevent the second gimbal link from interfering with the first gimbal link, and
   the interference prevention control is stopped when the operation unit is stopped.

2. The input device of a surgical manipulator according to claim 1, wherein the controller is configured to determine whether the operation unit is operated, and to perform the interference prevention control upon determination that the operation unit is operated.

3. The input device of a surgical manipulator according to claim 1, wherein the controller is configured to determine whether the follower link is within a predetermined operation range, and to perform the interference prevention control upon determination that the follower link is within the predetermined operation range.

4. The input device of a surgical manipulator according to claim 1, wherein the controller is configured to perform feedforward control of adding a rotation speed of the second gimbal link to a speed command in the interference prevention control of the rotation position of the follower link.

5. The input device of a surgical manipulator according to claim 4, wherein the controller is configured to determine whether the follower link is within a predetermined operation range, and to perform the feedforward control upon determination that the follower link is within the predetermined operation range.

6. The input device of a surgical manipulator according to claim 5, wherein the controller is configured to adjust an addition amount of a rotation speed of the second gimbal link to a speed command in the interference prevention control to gradually decrease as the follower link goes toward a predetermined operation range limit of the follower link, near the predetermined operation range limit of the follower link in the feedforward control.

7. The input device of a surgical manipulator according to claim 5, wherein the controller is configured to adjust an addition amount of a rotation speed of the second gimbal link to a speed command in the interference prevention control to decrease toward zero as an absolute value of a rotation position deviation with respect to the first reference rotation position of a rotation position of the first gimbal link approaches 90 degrees from 0 degrees in the feedforward control.

8. The input device of a surgical manipulator according to claim 1, wherein the controller is configured to perform interference prevention control to prevent the second gimbal link from interfering with the first gimbal link by maintaining a right angle between the first gimbal link and the second gimbal link.

9. A robot-assisted surgical system comprising:
   a manipulator having a distal end to which a surgical tool is attached; and
   an input device that operates the manipulator,
   wherein the input device includes
   an arm unit having a joint,
   a wrist unit including a follower link having a base end rotatably connected to a distal end of the arm unit around a follower rotation axis, a first gimbal link having a base end rotatably connected to a distal end of the follower link and rotatable with respect to a first reference rotation position around a first gimbal rotation axis orthogonal to the follower rotation axis, a second gimbal link having a base end rotatably connected to a distal end of the first gimbal link and rotatable with respect to a second reference rotation position around a second gimbal rotation axis that is orthogonal to the first gimbal rotation axis, the first reference rotation position of the first gimbal link corresponding to a position in which the second gimbal rotation axis coincides with the follower rotation axis, and an operation unit as a third gimbal link having a base end rotatably connected to a distal end of the second gimbal link around a third gimbal rotation axis that is orthogonal to the second gimbal rotation axis, the second reference rotation position of the second gimbal link corresponding to a position in which the third gimbal axis is orthogonal to the first gimbal rotation axis, a motor that rotates the base end of the follower link around the follower rotation axis, and a controller configured to perform interference prevention control of a rotation position of the follower link to maintain the second rotation position of the second gimbal link using a rotation position deviation between a rotation position of the second gimbal link and the second reference rotation position as a rotation position deviation of the follower link by controlling an operation of the motor, wherein the interference prevention control is performed only when the operation unit is operated to maintain the second rotation position by maintaining orthogonality between the first gimbal rotation axis and the third gimbal rotation axis to prevent the second gimbal link from interfering with the first gimbal link, and the interference prevention control is stopped when the operation unit is stopped.

10. The robot-assisted surgical system according to claim 9, wherein the controller is configured to determine whether the operation unit is operated, and to perform the interference prevention control upon determination that the operation unit is operated.

11. The robot-assisted surgical system according to claim 9, wherein the controller is configured to determine whether the follower link is within a predetermined operation range, and to perform the interference prevention control upon determination that the follower link is within the predetermined operation range.

12. The robot-assisted surgical system according to claim 9, wherein the controller is configured to perform feedforward control of adding a rotation speed of the second gimbal link to a speed command in the interference prevention control of the rotation position of the follower link.

13. The robot-assisted surgical system according to claim 12, wherein the controller is configured to determine whether the follower link is within a predetermined operation range, and to perform the feedforward control upon determination that the follower link is within the predetermined operation range.

14. The robot-assisted surgical system according to claim 13, wherein the controller is configured to adjust an addition amount of a rotation speed of the second gimbal link to a speed command in the interference prevention control to gradually decrease as the follower link goes toward a predetermined operation range limit of the follower link, near the predetermined operation range limit of the follower link in the feedforward control.

15. The robot-assisted surgical system according to claim 13, wherein the controller is configured to adjust an addition amount of a rotation speed of the second gimbal link to a speed command in the interference prevention control to decrease toward zero as an absolute value of a rotation position deviation with respect to the first reference rotation position of a rotation position of the first gimbal link approaches 90 degrees from 0 degrees in the feedforward control.

16. The robot-assisted surgical system according to claim 9, further comprising a positioner that supports the manipulator, wherein the positioner includes an articulated robot.

17. The robot-assisted surgical system according to claim 16, further comprising a second manipulator having a distal end to which a second surgical tool is attached, wherein the positioner supports the manipulator and the second manipulator.

18. A controller configured to control an input device that operates a manipulator having a distal end to which a surgical tool is attached, wherein the input device includes an arm unit having a joint, a wrist unit including a follower link having a base end rotatably connected to a distal end of the arm unit around a follower rotation axis, a first gimbal link having a base end rotatably connected to a distal end of the follower link and rotatable with respect to a first reference rotation position around a first gimbal rotation axis orthogonal to the follower rotation axis, a second gimbal link having a base end rotatably connected to a distal end of the first gimbal link and rotatable with respect to a second reference rotation position around a second gimbal rotation axis that is orthogonal to the first gimbal rotation axis, the first reference rotation position of the first gimbal link corresponding to a position in which the second gimbal rotation axis coincides with the follower rotation axis, and an operation unit as a third gimbal link having a base end rotatably connected to a distal end of the second gimbal link around a third gimbal rotation axis that is orthogonal to the second gimbal rotation axis, the second reference rotation position of the second gimbal link corresponding to a position in which the third gimbal axis is orthogonal to the first gimbal rotation axis, and a motor that rotates the base end of the follower link around the follower rotation axis, the controller is configured to perform interference prevention interference prevention control of a rotation position of the follower link to maintain the second rotation position of the second gimbal link using a rotation position deviation between a rotation position of the second gimbal link and the second reference rotation position as a rotation position deviation of the follower link by controlling an operation of the motor, the interference prevention control is performed only when the operation unit is operated to maintain the second rotation position by maintaining orthogonality between the first gimbal rotation axis and the third gimbal rotation axis to prevent the second gimbal link from interfering with the first gimbal link, and the interference prevention control is stopped when the operation unit is stopped.

19. The controller according to claim 18, configured to determine whether the operation unit is operated, and to perform the interference prevention control upon determination that the operation unit is operated.

20. The controller according to claim 18, configured to determine whether the follower link is within a predetermined operation range, and to perform the interference prevention control upon determination that the follower link is within the predetermined operation range.

21. The controller according to claim 18, configured to perform feedforward control of adding a rotation speed of the second gimbal link to a speed command in the interference prevention control of the rotation position of the follower link.

22. An input device of a surgical manipulator, the input device comprising:

an arm unit having a joint;

a wrist unit including a follower link having a base end rotatably connected to a distal end of the arm unit around a follower rotation axis, a first gimbal link having a base end rotatably connected to a distal end of the follower link and rotatable with respect to a first reference rotation position around a first gimbal rotation axis orthogonal to the follower rotation axis, a second gimbal link having a base end rotatably connected to a distal end of the first gimbal link and rotatable with respect to a second reference rotation position around a second gimbal rotation axis that is orthogonal to the first gimbal rotation axis, the first reference rotation position of the first gimbal link corresponding to a position in which the second gimbal rotation axis coincides with the follower rotation axis, and an operation unit as a third gimbal link having a base end rotatably connected to a distal end of the second gimbal link around a third gimbal rotation axis that is orthogonal to the second gimbal rotation axis, the second reference rotation position of the second gimbal link corresponding to a position in which the third gimbal axis is orthogonal to the first gimbal rotation axis;

a motor that rotates the base end of the follower link around the follower rotation axis; and a controller configured to perform interference prevention control of a rotation position of the follower link to maintain a second rotation position of the second gimbal link using a rotation position deviation between a rotation position of the second gimbal link and the second reference rotation position as a rotation position deviation of the follower link by controlling an operation of the motor, wherein the interference prevention control is performed only when the operation unit is operated to maintain the second rotation position by maintaining orthogonality between the first gimbal rotation axis and the third gimbal rotation axis to prevent the second gimbal link from interfering with the first gimbal link, and the rotation of the follower link is stopped when the operation unit is stopped even if a deviation in orthogonality remains between the first gimbal rotation axis and the third gimbal rotation axis.

* * * * *